US007005499B1

(12) United States Patent  
Lewin et al.

(10) Patent No.: US 7,005,499 B1  
(45) Date of Patent: Feb. 28, 2006

(54) WNT-REGULATED CYTOKINE-LIKE POLYPEPTIDE AND NUCLEIC ACIDS ENCODING SAME

(75) Inventors: David A. Lewin, New Haven, CT (US); Diane Pennica, Burlingame, CA (US); Luca Rastelli, Guilford, CT (US); Bruce Taillon, Middletown, CT (US)

(73) Assignees: Genentech, Inc., South San Francisico, CA (US); Curagen Corporation, New Haven, CT (US)

( * ) Notice: Subject to any disclaimer, the term of this patent is extended or adjusted under 35 U.S.C. 154(b) by 0 days.

(21) Appl. No.: 09/715,418

(22) Filed: Nov. 16, 2000

Related U.S. Application Data

(60) Provisional application No. 60/166,177, filed on Nov. 18, 1999.

(51) Int. Cl.  
   *C07K 14/47* (2006.01)
(52) U.S. Cl. .................................................. 530/350
(58) Field of Classification Search ............... 530/350, 530/325; 514/12  
See application file for complete search history.

(56) References Cited

U.S. PATENT DOCUMENTS 5,871,697 A    2/1999  Rothberg et al.  
6,117,989 A *  9/2000  Bandman et al. .......... 536/23.1

FOREIGN PATENT DOCUMENTS

| WO | WO 97/34013 | 9/1997 |
| WO | WO 99/47669 | 9/1999 |
| WO | WO 00/55173 | 9/2000 |
| WO | WO 01/00828 | 1/2001 |

OTHER PUBLICATIONS

Wang et al. mRNA differential display: application in the discovery of novel pharmacological targets. Trends Pharmacol Sci. Aug. 1996;17(8):276-9.*
Schafer et al. The S100 family of EF-hand calcium-binding proteins: functions and pathology. Trends Biochem Sci. Apr. 1996;21(4)134-40.*
Donato R. S100: a multigenic family of calcium-modulated proteins of the EF-hand type with intracellular and extracellular functional roles. Int J Biochem Cell Biol. Jul. 2001; 33(7):637-68.*
Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Haynes et al. Proteome analysis: biological assay or data archive? Electrophoresis. Aug. 1998;19(11):1862-71.*
Hancock WS. Do we have enough biomarkers? J Proteome Res. Jul.-Aug. 2004;3(4):685.*
Allman et al. BCL-6 expression during B-cell activation. Blood. Jun. 15, 1996;87(12):5257-68.*
Camby, I., F. Lefranc, et al., "Differential expression of S100 calcium-binding proteins characterizes distinct clinical entities in both WHO grade II and III astrocytic tumours", Neuropathology and Applied Neurobiology, 26 (2000), pp 76-90.
Dale, I., M. K. Fagerhol, et al., "Purification and partial characterization of a highly immunogenic human leukocyte protein, the L1 antigen", Euro J Biochem 134 (1983), pp 1-6.
De Ferrari, G. V. and N. C. Inestrosa, "Wnt signaling function in Alzheimer's disease", Brain Research Reviews 33 (2000), pp 1-12.
Djukanovic, D., U. Hofmann, et al., "Comparison of S100 protein and MIA protein as serum marker for malignant melanoma", Anticancer Research, 20 (2000), pp 2203-2208.
Donato, R., "Funcational roles of S100 proteins, calcium-binding proteins of the EF- hand type." Biochimica et Biophysica Acta 1450 (1999), pp 191-231.
Huang, X., "A contig assembly program based on sensitive detection of fragment overlaps" Genomics 14 (1992), pp 18-25.
Kerlavage, A.R, Direct Submission. GenBank Accession No.: AA315020, 1997, pp 1-2.
Kligman, D. and D. C. Hilt, "The S100 protein family", Trends Biochemistry Science 13 (1988), pp 437-443.
Kuhl, M., L. C. Sheldahl, et al., "The Wnt/Ca2+ pathway: a new vertebrate Wnt signaling pathway takes shape", Trends Genet 16 (2000), pp 279-283.
Nacken, W., C. Sopalla, et al., "Biochemical characterization of the murine S100A9 (MRP14) protein suggests that is functionally equivalent to its human counterpart despite its low degree of sequence homology", Eur J Biochem 267 (2000), pp 560-565.
Patapoutian, A. and L. F. Reichardt, "Roles of Wnt proteins in neural development and maintenance" Curr Opin Neurobiol 10 (2000), pp 392-399.
Peifer, M. and P. Polakis, "Wnt signaling in oncogenesis and embryogenesis—a look outside the nucleus", Science 287 (2000), pp 1606-1609.

(Continued)

*Primary Examiner*—David Romeo  
(74) *Attorney, Agent, or Firm*—Merchant & Gould P.C.

(57) ABSTRACT

The present invention provides novel polypeptides, termed FCTRX polypeptides, as well as polynucleotides encoding FCTRX polypeptides and antibodies that immunospecifically bind to an FCTRX or a derivative, variant, mutant, or fragment of an FCTRX polypeptide, polynucleotide or antibody. The invention additionally provides methods in which the FCTRX polypeptide, polynucleotide and antibody are used in detection and treatment of a broad range of pathological states, as well as to other uses.

7 Claims, 8 Drawing Sheets

OTHER PUBLICATIONS

Pietas, et al., "Human cDNA of a new member of the s100 protein family which is downregulated in lung carcinoma cells" Direct Submission. GenBank Accession No.: AY007220, 2000, pp. 1-2.

Sastry, M., R. R. Ketchem, et al., "The three-dimensional structure of Ca(2+)-bound calcyclin: implications for Ca (2+)-signal transduction by S100 proteins", Structure 6 (1998), pp 223-231.

Sheng, J. G., R. E. Mrak, et al., "Overexpression of the neuritotrophic cytokine S100beta precedes the appearance of neuritic beta-amyloid plaques in APPV717F mice", J Neurochem 74 (2000), pp 295-301.

Shimkets, R. A., D. G. Lowe, et al., "Gene expression analysis by transcript profiling coupled to a gene database query", Nature Biotechnology 17 (1999), pp 798-803.

Smalley, M. J. and T. C. Dale, "Wnt signalling in mammalian development and cancer" Cancer Metastasis Rev 18(1999), pp 1-2. (Abstract Only).

Xu, K. and C. L. Geczy, "IFN-gamma and TNF regulate macrophage expression of the chemotactic S100 protein S100A8", The Journal of Immunology, (2000), pp 4916-4923.

Adams, M.D. et al., "EST186826 HCC Cell Line (Metastasis to Liver in Mouse) II Homo Sapiens CDNA 5' End mRNA Sequence", Accession No.: AA315020, 1997, AND Adams, M.D. et al., "Initial Assessment of Human Gene Diversity and Expression Patterns Based Upon 83 Million Nucleotides of cDNA", *Nature*, vol. 377, 1995, pp 3-174.

Marra, M. et al., "The WashU-HMMI Mouse EST Project", Accession No.: W20659, 1996, nucleotides 1-1074.

Marra, M. et al., "The WashU-HHMI Mouse EST Project", Accession No.: W34209, 1997, nucleotides 166-377.

Marra, M. et al., "The WashU-HMMI Mouse EST Project", Accession No.: AA638675, 1997, nucleotides 175-386.

Marra, M. et al., "The WashU-HMMI Mouse EST Project", Accession No.: 726094, 1998, nucleotides 1-483.

Brown, A., "Commentary: Wnt signaling in breat cancer: have we come full circle?," *Breast Cancer Research*, vol. 3, No. 6, pp. 351-355 (2001).

Nusse, R. et al., "*Wnt Genes,*" *Cell*, vol. 69, pp. 1073-1087 (Jun. 26, 1992).

Tsukamoto, A. et al., "Expression of the int-1 Gene in Transgenic Mice Is Associated with Mammary Gland Hyperplasia and Adenocarcinomas in Male and Female Mice," *Cell*, vol. 5, pp. 619-625 (Nov. 18, 1988).

Wong, G. et al., "Differential Transformation of Mammary Epithelial Cells by Wnt Genes," *Molecular And Cellular Biology*, vol. 14, No. 9, pp. 6278-6286 (Sep. 1994).

* cited by examiner

Figure 1.

```
Sequence type explicitly set to Protein
Sequence format is Pearson
Sequence 1: new_S100_cytokine     104 aa
Sequence 2: G491246                110 aa
Sequence 3: W27152                  98 aa
Start of Pairwise alignments
Aligning...
Sequences (1:2) Aligned. Score:  23
Sequences (1:3) Aligned. Score:  34
Sequences (2:3) Aligned. Score:  29
Start of Multiple Alignment
There are 2 groups
Aligning...
Group 1:                     Delayed
Group 2:                     Delayed
Sequence:1      Score:0
Sequence:3      Score:839
Sequence:2      Score:724
Alignment Score 444
CLUSTAL-Alignment file created  [/data4/genetools/lrastelli4630clustalw]
```

Multiple Alignment:

```
new_S100_cytokine  MGQCRSANAEDAQEFSDVERAIETLIKNFHQYSVEGG-KETLTPSELRDLVTQQLPHLMP
W27152             ---------MAAEPLTELEESIETVVTFFTFARQEGRKDSLSVNFFKELVTQQLPHLLK
G491246            ---------------MSQLERNIETIINTFHQYSVKLGHPDTLNQGEFKELVRKDLQNFLK new_S100_cytokine  SNCG----LEEKIANLGSCNDSKLEFRSEWELIGEAAKSVKLERP----VRSH---(SEQ ID NO:6)
W27152             DVGS----LDEKMKSLDVNQDSELKFNEYWRLIGELAKEIRKKKD----LKIRKK-(SEQ ID NO:10)
G491246            KENKNEKVIEHIMEDLDTNADKQLSFEEFIMLMARLTWASHEKMHEGDEGPGHHHKPGLG new_S100_cytokine  ----
W27152             ----
G491246            EGTP (SEQ ID NO:11)
```

Figure 2.

Multiple Alignment:

```
new_S100_cytokine      ------------DNRTLTKGPDTVS-TMGQCRSANAEDAQEFSDVERAIETLIKNFHQYS
7971c.7___r0s0-212.2__EXT  SISSCGAGYRTDDKTQLTEGRTSVPGTMGQCRSANAEDAQEFSDVERAIETLIKNFHKYS new_S100_cytokine      VEGGKETLTPSELRDLVTQQLPHLMPSNCGLEEKIANLGSCNDSKLEFRSFWELIGEAAK
7971c.7___r0s0-212.2__EXT  VASKKETLTPAELRDLVTQQLPHLMPSNCGLEEKIANLGNCNDSKLEFGSFWELIGEAAK new_S100_cytokine      SVKLERPVRGH    (SEQ ID NO:6)
7971c.7___r0s0-212.2__EXT  SVKMERPVTRS    (SEQ ID NO:3)
```

Figure 3.

```
hmmpfam - search a single seq against HMM database

HMMER is freely distributed under the GNU General Public License (GPL).
- - - - - - - - - - - - - - - - - - - - - - - - - - - - - - - - - - - -
HMM file:              pfamHMMs
Sequence file:         /data4/genetools/lrastelli4423Aa315020ProteinFasta.txt
- - - - - - - - - - - - - - - - - - - - - - - - - - - - - - - - - - - -
Query:  AA315020

Scores for sequence family classification (score includes all domains):
Model     Description                                       Score    E-value  N
--------  -----------                                       -----    -------  ---
S_100     S-100/ICaBP type calcium binding domain            40.9    2.9e-08  1

Parsed for domains:
Model     Domain  seq-f  seq-t     hmm-f  hmm-t      score   E-value
--------  ------  -----  -----     -----  -----      -----   -------
S_100     1/1        32     74 ..      1     44 []    40.9   2.9e-08

Alignments of top-scoring domains:
S_100: domain 1 of 1, from 32 to 74: score 40.9, E = 2.9e-08
                  *->LEkaietiInvFhqYSgreGdkdtLsKkELKeLlekELpnfLkn<-*
                     E+aiet+I+  FhqYS  eG k tL+   EL+ L++++Lp+ +
     AA315020   32    VERAIETLIKNFHQYS-VEGGKETLTPSELRDLVTQQLPHLMPS    74(SEQ ID NO:35)

//
```

BLOCKS Protein Domain Analysis of new_S100_cytokine

| | | SEQ ID NO |
|---|---|---|
| sNCGLIEKiaNLg3CnDSKLefRSfWeLIGEAAXsVk | (SEQ ID NO:12) |
| DvERAIETLIKrfHqYSVEgGKeTltpsElrdLvtQQ | (SEQ ID NO:13) |
| VTQQlpHLMpSncgLEEki | (SEQ ID NO:14) |
| AnaEDAQEFs | (SEQ ID NO:15) |
| GGkDtlTpselRD1vTQQlpHLmpsntgleEkiANlgScndSkleFRsf | (SEQ ID NO:16) |
| mgQcRSAnAedAQefSdVERaIEtlIKN

Figure 4B

```
                        10         20         30         40         50         60
                ....|....|....|....|....|....|....|....|....|....|....|....|
Table 3         MGQCRSANAEDAQEFSDVERAIETLIKNFHKYSVAGKKETLTPAELRDLVTQQLPHLMPS
AY007220        MGQCRSANAEDAQEFSDVERAIETLIKNFHQYSVEGGKETLTPSELRDLVTQQLPHLMPS
Consensus       MGQCRSANAEDAQEFSDVERAIETLIKNFH YSV   KETLTP ELRDLVTQQLPHLMPS 70         80         90        100
                ....|....|....|....|....|....|....|....|....|..    (amino acids 28-129 of
Table 3         NCGLEEKIANLGNCNDSKLEFGSFWELIGEAAKSVKMERPV         SEQ ID NO:3)
AY007220        NCGLEEKIANLGSCNDSKLEFRSFWELIGEAAKSVKLERPV         (SEQ ID NO:39) (1-101)
Consensus       NCGLEEKIANLG CNDSKLEF SFWELIGEAAKSVK ERPV         (SEQ ID NO:40)
```

Figure 4C

```
                        10         20         30         40         50         60
                ....|....|....|....|....|....|....|....|....|....|....|....|
Table 6         MGQCRSANAEDAQEFSDVERAIETLIKNFHQYSVEGGKETLTPSELRDLVTQQLPHLMPS
AY007220        MGQCRSANAEDAQEFSDVERAIETLIKNFHQYSVEGGKETLTPSELRDLVTQQLPHLMPS
Consensus       MGQCRSANAEDAQEFSDVERAIETLIKNFHQYSVEGGKETLTPSELRDLVTQQLPHLMPS 70         80         90        100
                ....|....|....|....|....|....|....|....|....|.....   (amino acids 15-118 of
Table 6         NCGLEEKIANLGSCNDSKLEFRSFWELIGEAAKSVKLERPVRGH         SEQ ID NO:6)
AY007220        NCGLEEKIANLGSCNDSKLEFRSFWELIGEAAKSVKLERPVRGH         (SEQ ID NO:39)
Consensus       NCGLEEKIANLGSCNDSKLEFRSFWELIGEAAKSVKLERPVRGH         (SEQ ID NO:49)
```

Figure 4D

```
                                10         20         30         40
                        ....|....|....|....|....|....|....|....|....|   (amino acids 46-85 of
Table 3                 ERAIETLIKNFHKYSV-AGKKETLTPAELRDLVTQQLPHLM       SEQ ID NO:3)
gi|4139958|pdb|1MHO     EKAVVALIDVFHQYSGREGDKHKLKKSELKELINNELSHEL       (SEQ ID NO:41)
PROTEIN MRP-126         EKAIDVIIDVFHQYSRREGDKDTLTRKELKLLDPKQLANYL       (SEQ ID NO:42)
ICTACALCIN              QKGMALLISTFHKYSGKEGDKCTLTKGELKDLLTKELGGAF       (SEQ ID NO:43)
CALGRANULIN B           ESSIETIINIFHQYSVRLGHYDTLIQKEFKQLVQKELPNEL       (SEQ ID NO:44)
Consensus                   I   FH YS   G      L  E    L       L        (SEQ ID NO:45)
```

Figure 4E

```
                                10         20         30         40
                        ....|....|....|....|....|....|....|....|....|   (amino acids 33-72 of
Table 6                 ERAIETLIKNFHQYSV-EGGKETLTPSELRDLVTQQLPHLM       SEQ ID NO:6)
gi|4139958|pdb|1MHO     EKAVVALIDVFHQYSGREGDKHKLKKSELKELINNELSHFL       (SEQ ID NO:41)
PROTEIN MRP-126         EKAIDVIIDVFHQYSRREGDKDTLTRKELKLLDPKQLANYL       (SEQ ID NO:42)
CALGRANULIN B           ESSIETIINIFHQYSVRLGHYDTLIQKEFKQLVQKELPNEL       (SEQ ID NO:44)
CALGRANULIN B           ERSITTIIDTFHQYSRREGHPDTLSKKEFRQMVEQLATEM       (SEQ ID NO:46)
Consensus                   I   FHQYS          L  E    L       L        (SEQ ID NO:47)
```

Figure 7

| | **********************Contig 1********************************** |
|---|---|
| 65677221+ | GAATTCCAGAGGGAGTTCTCAGTGCCCCCGGACAGGCCTCTCCAGCTTCACACTCTTGGC |
| AA315020- | TGCCCCGGACAGTCCTCTCNAGCTTCACACTCTTGGC |
| consensus | GAATTCCAGAGGGAGTTCTCAGTGCCCCCGGACAGGCCTCTCCAGCTTCACACTCTTGGC |
| 65677221+ | CGCTTCTCCAATCAGCTCCCAGAAACTCCTGAACTCCAGTTTAGAGTCATTGCAGCTGCC |
| AA315020- | CGCTTCTCCAATCAGCTCCCAGAAACTCCTGAACTCCAGTTTAGAGTCATTGCAGCTGCC |
| consensus | CGCTTCTCCAATCAGCTCCCAGAAACTCCTGAACTCCAGTTTAGAGTCATTGCAGCTGCC |
| 65677221+ | CAGGTTGGCAATTTTCTCTTCCAGGCCACAGTTGCTCGGCATGAGATGGGGCAGCTGCTG |
| AA315020- | CAGGTTGGCAATTTTCTCTTCCAGGCCANAGTTGCTCGGCATGAGATGGGGCAGCTGCTG |
| consensus | CAGGTTGGCAATTTTCTCTTCCAGGCCACAGTTGCTCGGCATGAGATGGGGCAGCTGCTG |
| 65677221+ | GGTGACCAGGTCCCGTAGCTCAGAAGGGGTCAGCGTCTCCTTCCCACCCTCCACGGAGTA |
| AA315020- | GGTGACCAGGTCCCGTAGCTCAGAAGGGGTCAGCGTCTCCTTCCCACCCTCCACGGAGTA |
| consensus | GGTGACCAGGTCCCGTAGCTCAGAAGGGGTCAGCGTCTCCTTCCCACCCTCCACGGAGTA |
| 65677221+ | CTGGTGAAAGTTCTTGATGAGGGTCTCAATGGCCCCTCTCCACATCACTGAATTC (SEQ ID NO: 37) |
| AA315020- | CTGGTGAAAGTTCTTGATGAGGGTCTCAATGGCCCCTCTCCACATCACTGAATTCCTGAGC |
| consensus | CTGGTGAAAGTTCTTGATGAGGGTCTCAATGGCCCCTCTCCACATCACTGAATTCCTGAGC |
| AA315020- | ATCCTCTGCGTTGGCTGACCGACACTGTCCCATGGTGCTCACTGTGTCTGTGTCCTTTGGT |
| consensus | ATCCTCTGCGTTGGCTGACCGACACTGTCCCATGGTGCTCACTGTGTCTGTGTCCTTTGGT |
| AA315020- | GAGAGTTCTGTTGTCCTAT (SEQ ID NO: 48) |
| consensus | GAGAGTTCTGTTGTCCTAT (SEQ ID NO: 5) |

SEQUENCE LISTING

<160> NUMBER OF SEQ ID NOS: 49

<210> SEQ ID NO 1
<211> LENGTH: 212
<212> TYPE: DNA
<213> ORGANISM: Mus sp.

<400> SEQUENCE: 1

```
gaattcagtg atgtagagag ggccattgag acactcatca agaacttcca taaatactct      60
gtggcgggta aaaaggaaac actgaccct gctgagcttc gagacctggt tacccagcag     120
ctgccacacc tcatgccgag caactgtggg ttagaagaga aaattgccaa cctgggcaac    180
tgtaatgact cgaaactgga gtttggaagc tt                                   212
```

<210> SEQ ID NO 2
<211> LENGTH: 1670
<212> TYPE: DNA
<213> ORGANISM: Mus sp.
<220> FEATURE:
<221> NAME/KEY: misc_feature
<222> LOCATION: (1541)
<223> OTHER INFORMATION: "n" represents a, t, c, g, other or unknown

<400> SEQUENCE: 2

```
tcaggtgagc tggctcctcc atcctgtctc ccagctgcca gcaggtctcc ccctcctcta      60
ggtagatcat gatccatcag ctcctgtggg gcaggctata ggacagacga caaaactcaa    120
ctcacagaag gaaggaccag tgtaccagga acgatgggac agtgtcggtc agccaatgct    180
gaggatgccc aagaattcag tgatgtagag agggccattg agacactcat caagaacttc    240
cataaatact ctgtggcggg taaaaaggaa acactgaccc ctgctgagct tcgagacctg    300
gttacccagc agctgccaca cctcatgccg agcaactgtg ggttagaaga gaaaattgcc    360
aacctgggca actgtaatga ctcgaaactg gagtttggaa gcttctggga gttgattgga    420
gaagcagcca agagtgtgaa gatggagagg cctgttactc ggagctgagg acttctactt    480
ggaacttgtt gggggtgttg gggataggg agttttagag gcactggaaa taaaaccctc    540
aatgcccacc accccttcc ccagcctgca cctctcctca ttgctgcaat gttcacgttc    600
aggacaggct tccctgtggg ctccatggag ctcctgggtc cagaagtcct catctcaagg    660
gagctcaggg ggtgggttgg ggctggagag gatatgcagg gatcctggaa gggtaagggc    720
caagcaattt ggtagtaggg gaagggcaga aaggaactgg gttatggaag tgatccaaag    780
agcagggatg ggaatctggc tgcatatttg gtcctgaaaa gggtgtctga gaacctaccc    840
ccttctaatc ttgtcccacc taaactgtag ttgtctgccc tgtgctatcc ttgctgcttc    900
```

-continued

```
cagctctgcc ccatcctcct tccagtgtct gttcctgagt aggggcaggg gaaataggag      960
cagagttgca aaagaggctg aggagggcat gacttcatca ctttggggtg agaggaccag     1020
ctagatgctt gggcatttat ggtagttatt ttatatcatt tgattaataa aaatattgga     1080
aaatgtaaag aaaaaaaaag aaaaaaacat ggggccgaaa ccttatcccc cttgagtagg     1140
gtgatatttt gcgtgtgcaa tgggcggcct gttttcgaga ggcggtgaca tggggaaaac     1200 atggggtgt accaaacctt aaccgccttt taggggaaac accccttttg ccgcaagtgg      1260
gttaataacg gaagaagccc ggccggattg cccttcacaa gagtctcccg cggtagatgc     1320
ggatgggaca gcccccttcg gcggcgttta gagcggcgtg tgtgtggttt ctacgcgaat     1380
agggataaat attgtggcgg cgccgaggga gtgtgtgtgt tgcgcgcctg cttctgtgga     1440
ggtggtgtgt cccaaaaact aaaagggccc ttttgtgcgc gttagtttgc tctagcagag     1500
tccgctgcac atattttggt gggcgtgtcc gtgccgcccg nggtggtgct tgttgctggc     1560
gtggcgtggg gtgggtgtgg ttgcgggggt ggtcgtgttg ggtgtgtgcg tgcgcgcggg     1620
ggccgtgtgt gtgtgtggtt gcatgataag gttagagtga gtgagagcgg              1670
```

<210> SEQ ID NO 3
<211> LENGTH: 131
<212> TYPE: PRT
<213> ORGANISM: Mus sp.

<400> SEQUENCE: 3

```
Ser Ile Ser Ser Cys Gly Ala Gly Tyr Arg Thr Asp Asp Lys Thr Gln
 1               5                  10                  15

Leu Thr Glu Gly Arg Thr Ser Val Pro Gly Thr Met Gly Gln Cys Arg
            20                  25                  30

Ser Ala Asn Ala Glu Asp Ala Gln Glu Phe Ser Asp Val Glu Arg Ala
        35                  40                  45

Ile Glu Thr Leu Ile Lys Asn Phe His Lys Tyr Ser Val Ala Gly Lys
    50                  55                  60

Lys Glu Thr Leu Thr Pro Ala Glu Leu Arg Asp Leu Val Thr Gln Gln
65                  70                  75                  80

Leu Pro His Leu Met Pro Ser Asn Cys Gly Leu Glu Glu Lys Ile Ala
                85                  90                  95

Asn Leu Gly Asn Cys Asn Asp Ser Lys Leu Glu Phe Gly Ser Phe Trp
            100                 105                 110

Glu Leu Ile Gly Glu Ala Ala Lys Ser Val Lys Met Glu Arg Pro Val
        115                 120                 125

Thr Arg Ser
    130
```

<210> SEQ ID NO 4
<211> LENGTH: 357
<212> TYPE: DNA
<213> ORGANISM: Homo sapiens
<220> FEATURE:
<221> NAME/KEY: misc_feature
<222> LOCATION: (231)
<223> OTHER INFORMATION: "n" represents a, t, c, g, other or unknown
<220> FEATURE:
<221> NAME/KEY: misc_feature
<222> LOCATION: (337)
<223> OTHER INFORMATION: "n" represents a, t, c, g, other or unknown

<400> SEQUENCE: 4

```
ataggacaac agaactctca ccaaaggacc agacacagtg agcaccatgg gacagtgtcg      60
```

```
gtcagccaac gcagaggatg ctcaggaatt cagtgatgtg gagagggcca ttgagaccct    120
catcaagaac tttcaccagt actccgtgga gggtgggaag gagacgctga ccccttctga    180
gctacgggac ctggtcaccc agcagctgcc ccatctcatg ccgagcaact ntggcctgga    240
agagaaaatt gccaacctgg gcagctgcaa tgactctaaa ctggagttca ggagtttctg    300
ggagctgatt ggagaagcgg ccaagagtgt gaagctngag aggactgtcc gggggca       357
```

<210> SEQ ID NO 5
<211> LENGTH: 379
<212> TYPE: DNA
<213> ORGANISM: Homo sapiens

<400> SEQUENCE: 5

```
gaattccaga gggagttctc agtgcccccg gacaggcctc tccagcttca cactcttggc     60
cgcttctcca atcagctccc agaaactcct gaactccagt ttagagtcat tgcagctgcc    120
caggttggca attttctctt ccaggccaca gttgctcggc atgagatggg gcagctgctg    180
ggtgaccagg tcccgtagct cagaaggggt cagcgtctcc ttcccaccct ccacggagta    240
ctggtgaaag ttcttgatga gggtctcaat ggccctctcc acatcactga attcctgagc    300
atcctctgcg ttggctgacc gacactgtcc catggtgctc actgtgtctg gtcctttggt    360
gagagttctg ttgtcctat                                                 379
```

<210> SEQ ID NO 6
<211> LENGTH: 118
<212> TYPE: PRT
<213> ORGANISM: Homo sapiens

<400> SEQUENCE: 6

```
Asp Asn Arg Thr Leu Thr Lys Gly Pro Asp Thr Val Ser Thr Met Gly
  1               5                  10                  15

Gln Cys Arg Ser Ala Asn Ala Glu Asp Ala Gln Glu Phe Ser Asp Val
             20                  25                  30

Glu Arg Ala Ile Glu Thr Leu Ile Lys Asn Phe His Gln Tyr Ser Val
         35                  40                  45

Glu Gly Gly Lys Glu Thr Leu Thr Pro Ser Glu Leu Arg Asp Leu Val
     50                  55                  60

Thr Gln Gln Leu Pro His Leu Met Pro Ser Asn Cys Gly Leu Glu Glu
 65                  70                  75                  80

Lys Ile Ala Asn Leu Gly Ser Cys Asn Asp Ser Lys Leu Glu Phe Arg
                 85                  90                  95

Ser Phe Trp Glu Leu Ile Gly Glu Ala Ala Lys Ser Val Lys Leu Glu
            100                 105                 110

Arg Pro Val Arg Gly His
        115
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7

```
cttgatgagg gtctcaatgg                                                 20
```

<210> SEQ ID NO 8
<211> LENGTH: 26

-continued

```
<212> TYPE: DNA
<213> ORGANISM: Artificial Sequence
<220> FEATURE:
<223> OTHER INFORMATION: Description of Artificial Sequence: Probe

<400> SEQUENCE: 8
ccacatcact gaattcctga gcatcc                                          26

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
cagacacagt gagcaccatg                                                 20

<210> SEQ ID NO 10
<211> LENGTH: 98
<212> TYPE: PRT
<213> ORGANISM: Homo sapiens, W27152, chemotactic cytokine II CCII from
      WO97/34013

<400> SEQUENCE: 10

Met Ala Ala Glu Pro Leu Thr Glu Leu Glu Glu Ser Ile Glu Thr Val
 1               5                  10                  15

Val Thr Thr Phe Phe Thr Phe Ala Arg Gln Glu Gly Arg Lys Asp Ser
                20                  25                  30

Leu Ser Val Asn Glu Phe Lys Glu Leu Val Thr Gln Gln Leu Pro His
            35                  40                  45

Leu Leu Lys Asp Val Gly Ser Leu Asp Glu Lys Met Lys Ser Leu Asp
        50                  55                  60

Val Asn Gln Asp Ser Glu Leu Lys Phe Asn Glu Tyr Trp Arg Leu Ile
 65                  70                  75                  80

Gly Glu Leu Ala Lys Glu Ile Arg Lys Lys Lys Asp Leu Lys Ile Arg
                85                  90                  95

Lys Lys

<210> SEQ ID NO 11
<211> LENGTH: 110
<212> TYPE: PRT
<213> ORGANISM: Homo sapiens, G491246, Macrophage Migration Inhibition
      Factor (MRP-14)

<400> SEQUENCE: 11

Met Ser Gln Leu Glu Arg Asn Ile Glu Thr Ile Ile Asn Thr Phe His
 1               5                  10                  15

Gln Tyr Ser Val Lys Leu Gly His Pro Asp Thr Leu Asn Gln Gly Glu
                20                  25                  30

Phe Lys Glu Leu Val Arg Lys Asp Leu Gln Asn Phe Leu Lys Lys Glu
            35                  40                  45

Asn Lys Asn Glu Lys Val Ile Glu His Ile Met Glu Asp Leu Asp Thr
        50                  55                  60

Asn Ala Asp Lys Gln Leu Ser Phe Glu Glu Phe Ile Met Leu Met Ala
 65                  70                  75                  80

Arg Leu Thr Trp Ala Ser His Glu Lys Met His Glu Gly Asp Glu Gly
                85                  90                  95

Pro Gly His His His Lys Pro Gly Leu Gly Glu Gly Thr Pro
            100                 105                 110
```

<210> SEQ ID NO 12
<211> LENGTH: 37
<212> TYPE: PRT
<213> ORGANISM: Unknown Organism
<220> FEATURE:
<223> OTHER INFORMATION: Description of Unknown Organism: 3-100/ICaBP
      type calcium binding protein

<400> SEQUENCE: 12

Ser Asn Cys Gly Leu Glu Glu Lys Ile Ala Asn Leu Gly Ser Cys Asn
 1               5                  10                  15

Asp Ser Lys Leu Glu Phe Arg Ser Phe Trp Glu Leu Ile Gly Glu Ala
            20                  25                  30

Ala Lys Ser Val Lys
         35

<210> SEQ ID NO 13
<211> LENGTH: 37
<212> TYPE: PRT
<213> ORGANISM: Unknown Organism
<220> FEATURE:
<223> OTHER INFORMATION: Description of Unknown Organism: 3-100/ICaBP
      type calcium binding protein

<400> SEQUENCE: 13

Asp Val Glu Arg Ala Ile Glu Thr Leu Ile Lys Asn Phe His Gln Tyr
 1               5                  10                  15

Ser Val Glu Gly Gly Lys Glu Thr Leu Thr Pro Ser Glu Leu Arg Asp
            20                  25                  30

Leu Val Thr Gln Gln
         35

<210> SEQ ID NO 14
<211> LENGTH: 19
<212> TYPE: PRT
<213> ORGANISM: Unknown Organism
<220> FEATURE:
<223> OTHER INFORMATION: Description of Unknown Organism: Bacterial type
      II secretion system protein F

<400> SEQUENCE: 14

Val Thr Gln Gln Leu Pro His Leu Met Pro Ser Asn Cys Gly Leu Glu
 1               5                  10                  15

Glu Lys Ile

<210> SEQ ID NO 15
<211> LENGTH: 10
<212> TYPE: PRT
<213> ORGANISM: Unknown Organism
<220> FEATURE:
<223> OTHER INFORMATION: Description of Unknown Organism: Ubiquitin
      carboxyl-terminal hydrolases family

<400> SEQUENCE: 15

Ala Asn Ala Glu Asp Ala Gln Glu Phe Ser
 1               5                  10

<210> SEQ ID NO 16
<211> LENGTH: 49
<212> TYPE: PRT
<213> ORGANISM: Unknown Organism
<220> FEATURE:
<223> OTHER INFORMATION: Description of Unknown Organism: Bacterial
      themotaxis sensory transducers protein -continued

<400> SEQUENCE: 16

Gly Gly Lys Glu Thr Leu Thr Pro Ser Glu Leu Arg Asp Leu Val Thr
1               5                   10                  15

Gln Gln Leu Pro His Leu Met Pro Ser Asn Cys Gly Leu Glu Glu Lys
            20                  25                  30

Ile Ala Asn Leu Gly Ser Cys Asn Asp Ser Lys Leu Glu Phe Arg Ser
        35                  40                  45

Phe

<210> SEQ ID NO 17
<211> LENGTH: 32
<212> TYPE: PRT
<213> ORGANISM: Unknown Organism
<220> FEATURE:
<223> OTHER INFORMATION: Description of Unknown Organism:
      Phosphoenolpyruvate carboxykinase (ATP) protein

<400> SEQUENCE: 17

Met Gly Gln Cys Arg Ser Ala Asn Ala Glu Asp Ala Gln Glu Phe Ser
1               5                   10                  15

Asp Val Glu Arg Ala Ile Glu Thr Leu Ile Lys Asn Phe His Gln Tyr
            20                  25                  30

<210> SEQ ID NO 18
<211> LENGTH: 33
<212> TYPE: PRT
<213> ORGANISM: Unknown Organism
<220> FEATURE:
<223> OTHER INFORMATION: Description of Unknown Organism:
      Prokaryotic-type carbonic anhydrases proteins

<400> SEQUENCE: 18

His Gln Tyr Ser Val Glu Gly Gly Lys Glu Thr Leu Thr Pro Ser Glu
1               5                   10                  15

Leu Arg Asp Leu Val Thr Gln Gln Leu Pro His Leu Met Pro Ser Asn
            20                  25                  30

Cys

<210> SEQ ID NO 19
<211> LENGTH: 15
<212> TYPE: PRT
<213> ORGANISM: Unknown Organism
<220> FEATURE:
<223> OTHER INFORMATION: Description of Unknown Organism: Ergosterol
      biosynthesis ERG4/ERG24 family protein

<400> SEQUENCE: 19

Ile Ala Asn Leu Gly Ser Cys Asn Asp Ser Lys Leu Glu Phe Arg
1               5                   10                  15

<210> SEQ ID NO 20
<211> LENGTH: 25
<212> TYPE: PRT
<213> ORGANISM: Unknown Organism
<220> FEATURE:
<223> OTHER INFORMATION: Description of Unknown Organism:
      Lysosome-associated membrane glycoproteins du

<400> SEQUENCE: 20

Leu Met Pro Ser Asn Cys Gly Leu Glu Glu Lys Ile Ala Asn Leu Gly
1               5                   10                  15

Ser Cys Asn Asp Ser Lys Ile Glu Phe
            20                  25

```
                20                  25

<210> SEQ ID NO 21
<211> LENGTH: 39
<212> TYPE: PRT
<213> ORGANISM: Unknown Organism
<220> FEATURE:
<223> OTHER INFORMATION: Description of Unknown Organism:
      Phosphofructokinase proteins

<400> SEQUENCE: 21

Pro Ser Asn Cys Gly Leu Glu Glu Lys Ile Ala Asn Leu Gly Ser Cys
 1               5                  10                  15

Asn Asp Ser Lys Leu Glu Phe Arg Ser Phe Trp Glu Leu Ile Gly Glu
                20                  25                  30

Ala Ala Lys Ser Val Lys Leu
            35

<210> SEQ ID NO 22
<211> LENGTH: 10
<212> TYPE: PRT
<213> ORGANISM: Unknown Organism
<220> FEATURE:
<223> OTHER INFORMATION: Description of Unknown Organism: PH domain
      proteins profile

<400> SEQUENCE: 22

Pro Ser Asn Cys Gly Leu Glu Glu Lys Ile
 1               5                  10

<210> SEQ ID NO 23
<211> LENGTH: 45
<212> TYPE: PRT
<213> ORGANISM: Unknown Organism
<220> FEATURE:
<223> OTHER INFORMATION: Description of Unknown Organism: Myotoxins
      protein

<400> SEQUENCE: 23

Gln Gln Leu Pro His Leu Met Pro Ser Asn Cys Gly Leu Glu Glu Lys
 1               5                  10                  15

Ile Ala Asn Leu Gly Ser Cys Asn Asp Ser Lys Leu Glu Phe Arg Ser
                20                  25                  30

Phe Trp Glu Leu Ile Gly Glu Ala Ala Lys Ser Val Lys
            35                  40                  45

<210> SEQ ID NO 24
<211> LENGTH: 17
<212> TYPE: PRT
<213> ORGANISM: Unknown Organism
<220> FEATURE:
<223> OTHER INFORMATION: Description of Unknown Organism:
      Phosphatidylinositol-specific phospholipase X

<400> SEQUENCE: 24

Met Pro Ser Asn Cys Gly Leu Glu Glu Lys Ile Ala Asn Leu Gly Ser
 1               5                  10                  15

Cys

<210> SEQ ID NO 25
<211> LENGTH: 45
<212> TYPE: PRT
<213> ORGANISM: Unknown Organism
<220> FEATURE:
<223> OTHER INFORMATION: Description of Unknown Organism: Glypicans
``` protein

<400> SEQUENCE: 25

Met Gly Gly Cys Arg Ser Ala Asn Ala Glu Asp Ala Gln Glu Phe Ser
1               5                   10                  15

Asp Val Glu Arg Ala Ile Glu Thr Leu Ile Lys Asn Phe His Gln Tyr
            20                  25                  30

Ser Val Glu Gly Gly Lys Glu Thr Leu Thr Pro Ser Glu
        35                  40                  45

<210> SEQ ID NO 26
<211> LENGTH: 10
<212> TYPE: PRT
<213> ORGANISM: Unknown Organism
<220> FEATURE:
<223> OTHER INFORMATION: Description of Unknown Organism: Membrane
      attack complex components/perforin

<400> SEQUENCE: 26

Ile Lys Asn Phe His Gln Tyr Ser Val Glu
1               5                   10

<210> SEQ ID NO 27
<211> LENGTH: 44
<212> TYPE: PRT
<213> ORGANISM: Unknown Organism
<220> FEATURE:
<223> OTHER INFORMATION: Description of Unknown Organism: Urease nickel
      ligands protein

<400> SEQUENCE: 27

Thr Leu Ile Lys Asn Phe His Gln Tyr Ser Val Glu Gly Gly Lys Glu
1               5                   10                  15

Thr Leu Thr Pro Ser Glu Leu Arg Asp Leu Val Thr Gln Gln Leu Pro
            20                  25                  30

His Leu Met Pro Ser Asn Cys Gly Leu Glu Glu Lys
        35                  40

<210> SEQ ID NO 28
<211> LENGTH: 13
<212> TYPE: PRT
<213> ORGANISM: Unknown Organism
<220> FEATURE:
<223> OTHER INFORMATION: Description of Unknown Organism:
      Phosphoglycerate mutase family phosphohistidi

<400> SEQUENCE: 28

Gln Glu Phe Ser Asp Val Glu Arg Ala Ile Glu Thr Leu
1               5                   10

<210> SEQ ID NO 29
<211> LENGTH: 10
<212> TYPE: PRT
<213> ORGANISM: Unknown Organism
<220> FEATURE:
<223> OTHER INFORMATION: Description of Unknown Organism: Ribosomal
      protein L23 protein

<400> SEQUENCE: 29

Glu Leu Arg Asp Leu Val Thr Gln Gln Leu
1               5                   10

<210> SEQ ID NO 30
<211> LENGTH: 41
<212> TYPE: PRT

```
<213> ORGANISM: Unknown Organism
<220> FEATURE:
<223> OTHER INFORMATION: Description of Unknown Organism:
      2'-5'-oligoadenylate synthetases protein

<400> SEQUENCE: 30

Leu Glu Glu Lys Ile Ala Asn Leu Gly Ser Cys Asn Asp Ser Lys Leu
 1               5                  10                  15

Glu Phe Arg Ser Phe Trp Glu Leu Ile Gly Glu Ala Ala Lys Ser Val
            20                  25                  30

Lys Leu Glu Arg Pro Val Arg Gly His
        35                  40

<210> SEQ ID NO 31
<211> LENGTH: 24
<212> TYPE: PRT
<213> ORGANISM: Unknown Organism
<220> FEATURE:
<223> OTHER INFORMATION: Description of Unknown Organism: Formate and
      nitrite transporters protein

<400> SEQUENCE: 31

Asp Leu Val Thr Gln Gln Leu Pro His Leu Met Pro Ser Asn Cys Gly
 1               5                  10                  15

Leu Glu Glu Lys Ile Ala Asn Leu
            20

<210> SEQ ID NO 32
<211> LENGTH: 34
<212> TYPE: PRT
<213> ORGANISM: Unknown Organism
<220> FEATURE:
<223> OTHER INFORMATION: Description of Unknown Organism: Glycoprotein
      hormones beta chain protein

<400> SEQUENCE: 32

Gly Gln Cys Arg Ser Ala Asn Ala Glu Asp Ala Gln Glu Phe Ser Asp
 1               5                  10                  15

Val Glu Arg Ala Ile Glu Thr Leu Ile Lys Asn Phe His Gln Tyr Ser
            20                  25                  30

Val Glu

<210> SEQ ID NO 33
<211> LENGTH: 21
<212> TYPE: PRT
<213> ORGANISM: Unknown Organism
<220> FEATURE:
<223> OTHER INFORMATION: Description of Unknown Organism: Vinculin
      family talin-binding region protein

<400> SEQUENCE: 33

Lys Glu Thr Leu Thr Pro Ser Glu Leu Arg Asp Leu Val Thr Gln Gln
 1               5                  10                  15

Leu Pro His Leu Met
            20

<210> SEQ ID NO 34
<211> LENGTH: 40
<212> TYPE: PRT
<213> ORGANISM: Unknown Organism
<220> FEATURE:
<223> OTHER INFORMATION: Description of Unknown Organism:
      Beta-lactamases clas B protein

<400> SEQUENCE: 34
```

-continued

```
Ile Glu Thr Leu Ile Lys Asn Phe His Gln Tyr Ser Val Glu Gly Gly
  1               5                  10                  15

Lys Glu Thr Leu Thr Pro Ser Glu Leu Arg Asp Leu Val Thr Gln Gln
             20                  25                  30

Leu Pro His Leu Met Pro Ser Asn
         35                  40

<210> SEQ ID NO 35
<211> LENGTH: 21
<212> TYPE: PRT
<213> ORGANISM: Unknown Organism
<220> FEATURE:
<223> OTHER INFORMATION: Description of Unknown Organism: Heat shock
      hsp20 protein family profile

<400> SEQUENCE: 35

Leu Glu Phe Arg Ser Phe Trp Glu Leu Ile Gly Glu Ala Ala Lys Ser
  1               5                  10                  15

Val Lys Leu Glu Arg
             20

<210> SEQ ID NO 36
<211> LENGTH: 35
<212> TYPE: PRT
<213> ORGANISM: Unknown Organism
<220> FEATURE:
<223> OTHER INFORMATION: Description of Unknown Organism:
      Hydroxymethylglutaryl-coensyme A lyase protein

<400> SEQUENCE: 36

Met Gly Gly Cys Arg Ser Ala Asn Ala Glu Asp Ala Gln Glu Phe Ser
  1               5                  10                  15

Asp Val Glu Arg Ala Ile Glu Thr Leu Ile Lys Asn Phe His Gln Tyr
             20                  25                  30

Ser Val Glu
         35

<210> SEQ ID NO 37
<211> LENGTH: 294
<212> TYPE: DNA
<213> ORGANISM: Mus sp.

<400> SEQUENCE: 37
gaattccaga gggagttctc agtgcccccg gacaggcctc tccagcttca cactcttggc      60
cgcttctcca atcagctccc agaaactcct gaactccagt ttagagtcat tgcagctgcc    120
caggttggca attttctctt ccaggccaca gttgctcggc atgagatggg gcagctgctg    180
ggtgaccagg tcccgtagct cagaagggt cagcgtctcc ttcccaccct ccacggagta    240
ctggtgaaag ttcttgatga gggtctcaat ggccctctcc acatcactga attc            294

<210> SEQ ID NO 38
<211> LENGTH: 43
<212> TYPE: PRT
<213> ORGANISM: Homo sapiens

<400> SEQUENCE: 38

Val Glu Arg Ala Ile Glu Thr Leu Ile Lys Asn Phe His Gln Tyr Ser
  1               5                  10                  15

Val Glu Gly Gly Lys Glu Thr Leu Thr Pro Ser Glu Leu Arg Asp Leu
             20                  25                  30
```

Val Thr Gln Gln Leu Pro His Leu Met Pro Ser
            35                  40

<210> SEQ ID NO 39
<211> LENGTH: 104
<212> TYPE: PRT
<213> ORGANISM: Homo sapiens translation of GenBank Accession AAY007220

<400> SEQUENCE: 39

Met Gly Gln Cys Arg Ser Ala Asn Ala Glu Asp Ala Gln Glu Phe Ser
1               5                   10                  15

Asp Val Glu Arg Ala Ile Glu Thr Leu Ile Lys Asn Phe His Gln Tyr
            20                  25                  30

Ser Val Glu Gly Gly Lys Glu Thr Leu Thr Pro Ser Glu Leu Arg Asp
        35                  40                  45

Leu Val Thr Gln Gln Leu Pro His Leu Met Pro Ser Asn Cys Gly Leu
    50                  55                  60

Glu Glu Lys Ile Ala Asn Leu Gly Ser Cys Asn Asp Ser Lys Leu Glu
65                  70                  75                  80

Phe Arg Ser Phe Trp Glu Leu Ile Gly Glu Ala Ala Lys Ser Val Lys
                85                  90                  95

Leu Glu Arg Pro Val Arg Gly His
            100

<210> SEQ ID NO 40
<211> LENGTH: 94
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 40

Met Gly Gln Cys Arg Ser Ala Asn Ala Glu Asp Ala Gln Glu Phe Ser
1               5                   10                  15

Asp Val Glu Arg Ala Ile Glu Thr Leu Ile Lys Asn Phe His Tyr Ser
            20                  25                  30

Val Gly Lys Glu Thr Leu Thr Pro Glu Leu Arg Asp Leu Val Thr Gln
        35                  40                  45

Gln Leu Pro His Leu Met Pro Ser Asn Cys Gly Leu Glu Glu Lys Ile
    50                  55                  60

Ala Asn Leu Gly Cys Asn Asp Ser Lys Leu Glu Phe Ser Phe Trp Glu
65                  70                  75                  80

Leu Ile Gly Glu Ala Ala Lys Ser Val Lys Glu Arg Pro Val
                85                  90

<210> SEQ ID NO 41
<211> LENGTH: 41
<212> TYPE: PRT
<213> ORGANISM: Unknown Organism
<220> FEATURE:
<223> OTHER INFORMATION: Description of Unknown Organism:
      gi/4139958/pdb/1MHO

<400> SEQUENCE: 41

Glu Lys Ala Val Val Ala Leu Ile Asp Val Phe His Gln Tyr Ser Gly
1               5                   10                  15

Arg Glu Gly Asp Lys His Lys Leu Lys Lys Ser Glu Leu Lys Glu Leu
            20                  25                  30

Ile Asn Asn Glu Leu Ser His Phe Leu

```
<210> SEQ ID NO 42
<211> LENGTH: 41
<212> TYPE: PRT
<213> ORGANISM: Unknown Organism
<220> FEATURE:
<223> OTHER INFORMATION: Description of Unknown Organism: Protein
      MRP-126

<400> SEQUENCE: 42

Glu Lys Ala Ile Asp Val Ile Ile Asp Val Phe His Gln Tyr Ser Arg
 1               5                  10                  15

Arg Glu Gly Asp Lys Asp Thr Leu Thr Arg Lys Glu Leu Lys Leu Leu
            20                  25                  30

Ile Glu Lys Gln Leu Ala Asn Tyr Leu
            35                  40

<210> SEQ ID NO 43
<211> LENGTH: 41
<212> TYPE: PRT
<213> ORGANISM: Unknown Organism
<220> FEATURE:
<223> OTHER INFORMATION: Description of Unknown Organism: ICTACALCIN

<400> SEQUENCE: 43

Gln Lys Gly Met Ala Leu Leu Ile Ser Thr Phe His Lys Tyr Ser Gly
 1               5                  10                  15

Lys Glu Gly Asp Lys Cys Thr Leu Thr Lys Gly Glu Leu Lys Asp Leu
            20                  25                  30

Ile Thr Lys Glu Leu Gly Gly Ala Phe
            35                  40

<210> SEQ ID NO 44
<211> LENGTH: 41
<212> TYPE: PRT
<213> ORGANISM: Unknown Organism
<220> FEATURE:
<223> OTHER INFORMATION: Description of Unknown Organism: CALGRANULIN B

<400> SEQUENCE: 44

Glu Ser Ser Ile Glu Thr Ile Ile Asn Ile Phe His Gln Tyr Ser Val
 1               5                  10                  15

Arg Leu Gly His Tyr Asp Thr Leu Ile Gln Lys Glu Phe Lys Gln Leu
            20                  25                  30

Val Gln Lys Glu Leu Pro Asn Phe Leu
            35                  40

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 45

Ile Phe His Tyr Ser Gly Leu Glu Leu Leu
 1               5                  10

<210> SEQ ID NO 46
<211> LENGTH: 41
<212> TYPE: PRT
<213> ORGANISM: Unknown Organism
```

```
<220> FEATURE:
<223> OTHER INFORMATION: Description of Unknown Organism: CALGRANULIN B

<400> SEQUENCE: 46

Glu Arg Ser Ile Thr Thr Ile Ile Asp Thr Phe His Gln Tyr Ser Arg
 1               5                  10                  15

Lys Glu Gly His Pro Asp Thr Leu Ser Lys Lys Glu Phe Arg Gln Met
            20                  25                  30

Val Glu Ala Gln Leu Ala Thr Phe Met
        35                  40

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 47

Glu Ile Phe His Gln Tyr Ser Gly Leu Glu Leu
 1               5                  10

<210> SEQ ID NO 48
<211> LENGTH: 357
<212> TYPE: DNA
<213> ORGANISM: Artificial Sequence
<220> FEATURE:
<223> OTHER INFORMATION: Description of Unknown Organism: reverse strand
      sequence of SEQ ID NO:4 (GenBank AA315020)
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t

<400> SEQUENCE: 48
tgcccccgga cagtcctctc nagcttcaca ctcttggccg cttctccaat cagctcccag      60
aaactcctga actccagttt agagtcattg cagctgccca ggttggcaat tttctcttcc     120
aggccanagt tgctcggcat gagatggggc agctgctggg tgaccaggtc ccgtagctca     180 gaagggtca gcgtctcctt cccacccctcc acggagtact ggtgaaagtt cttgatgagg     240
gtctcaatgg ccctctccac atcactgaat tcctgagcat cctctgcgtt ggctgaccga     300
cactgtccca tggtgctcac tgtgtctggt cctttggtga gagttctgtt gtcctat        357

<210> SEQ ID NO 49
<211> LENGTH: 104
<212> TYPE: PRT
<213> ORGANISM: Artificial Sequence
<220> FEATURE:
<223> OTHER INFORMATION: Description of Artificial Sequence:  Consensus
      sequence

<400> SEQUENCE: 49

Met Gly Gln Cys Arg Ser Ala Asn Ala Glu Asp Ala Gln Glu Phe Ser
 1               5                  10                  15

Asp Val Glu Arg Ala Ile Glu Thr Leu Ile Lys Asn Phe His Gln Tyr
            20                  25                  30

Ser Val Glu Gly Gly Lys Glu Thr Leu Thr Pro Ser Glu Leu Arg Asp
        35                  40                  45
```

-continued

```
Leu Val Thr Gln Gln Leu Pro His Leu Met Pro Ser Asn Cys Gly Leu
     50                  55                  60
Glu Glu Lys Ile Ala Asn Leu Gly Ser Cys Asn Asp Ser Lys Leu Glu
 65                  70                  75                  80
Phe Arg Ser Phe Trp Glu Leu Ile Gly Glu Ala Ala Lys Ser Val Lys
                 85                  90                  95
Leu Glu Arg Pro Val Arg Gly His
             100
```

WNT-REGULATED CYTOKINE-LIKE POLYPEPTIDE AND NUCLEIC ACIDS ENCODING SAME

This application claims priority to U.S. Ser. No. 60/166,177, filed Nov. 18, 1999. The contents of this application are incorporated herein by reference in their entirety.

FIELD OF THE INVENTION

The invention relates in general to polynucleotides and polypeptides. The invention relates more particularly to polynucleotide sequences and the membrane-bound or secreted polypeptides encoded by such polynucleotides, as well as vectors, host cells, antibodies and recombinant methods for producing the polypeptides and polynucleotides.

BACKGROUND OF THE INVENTION

Wnt proteins are a family of secreted polypeptides that act through a signaling pathway, which is known as the Wnt signaling pathway. Previously described members of the Wnt signalling pathway include the putative Wnt receptor, which is encoded by members of the frizzled gene family. Other members of the Wnt-signalling pathway include the transcription factor beta-catenin, the adenomatous polyposis coli (APC) polypeptide, presenilin (PS), GSK-3b, Protein Phosphatase 2A proteins, the kinases CamKll and PKC, glycogen synthase kinase 3, the Dishevelled (Dvl) protein, and cyclins D1 and c-myc. Transcription of these latter genes is reported to be associated with activation of the Wnt signaling pathway. Interactions between some members of the Wnt-signaling pathway have been described. For example, APC is phosphorylated by GSK-3b, binds to beta-catenin and facilitates its degradation.

Wnt proteins control cell processes via at least two pathways. One of these, known as the "canonical" Wnt signaling pathway, operates through the cytosolic stabilization of beta-catenin (Smalley M J and Dale T C, 1999). Stabilization is achieved by downregulating the activity of a beta-catenin turnover complex. In the second pathway, activation of the Wnt signaling pathway stimulates intracellular Ca2+ release and activates the kinases CamKII and PKC (Kuhl et al. Trends Genet 2000 July:16(7):279–83).

Wnt signaling is involved in a variety of mammalian developmental processes, including cell proliferation, differentiation and epithelial-mesenchymal interactions (Smalley M J and Dale T C; Cancer Metastasis Rev 1999; 18(2):215–30). For example, Wnt signaling contributes to the development of tissues and organs such as the limbs, the brain, the reproductive tract and the kidney during embryognenesis (Peifer M and Polakis P, Science 2000 Mar 3;287 (5458):1606–9).

Constituents of Wnt signaling pathways are expressed in embroyogenesis and act in developing and mature nervous systems (Patapoutian A, and Reichards L F, Curr Opin Neurobiol 2000 June;10(3):392–9). For example, Wnt signaling is involved in the initial formation of the neural plate and in subsequent patterning decisions in the embryonic nervous system, including formation of the neural crest. Wnt signaling is also required at later stages of development.

Actions of members of the Wnt signaling pathway have also been associated with disease processes. For example, Wnt signaling has been demonstrated to regulate apoptosis and may participate in degenerative processes leading to cell death in the aging brain.

In addition, inappropriate activation of the canonical Wnt signaling pathway is reported to be a major feature in human neoplasia. Oncogenic activation of this pathway can occur in several ways. For example, mutations in either APC or beta-catenin have been associated with colon carcinomas. Inappropriate expression of Wnt and Wnt binding proteins has similarly been found in a variety of human tumors. Dysregulation of the beta-catenin turnover complex has been associated with several tumor types. Thus dysregulation can include in, e.g., loss of the Adenomatous Polyposis Coli (APC) or Protein Phosphatase 2A proteins, or activating mutations of beta-catenin.

Disruption of expression of members of the Wnt signaling pathway has also been associated with apoptosis and neurological conditions such as Alzheimer's disease (De Ferrari G V, and Inestrosa N C, Brain Res Brain Res Rev 2000 August:33(1):1–12).

SUMMARY OF THE INVENTION

The present invention is based in part upon the discovery of a nucleic acid sequence encoding a novel member of the Wnt signaling pathway. The novel member encodes a S100 cytokine-like polypeptide. The S100 cytokine-like nucleic acids and polypeptides encoded thereby are collectively referred to herein as "FCTRX".

Accordingly, in one aspect, the invention provides an isolated nucleic acid molecule that encodes a novel polypeptide, or a fragment, homolog, analog or derivative thereof. The nucleic acid can include, e.g., a nucleic acid sequence encoding a polypeptide at least 85% identical to a polypeptide comprising the amino acid sequences of SEQ ID NO: 3 or 6, or a polypeptide that is a fragment, homolog, analog or derivative thereof. The nucleic acid can include, e.g., one or more fragments from genomic DNA, or a cDNA molecule, or an RNA molecule. In particular embodiments, the nucleic acid molecule may include the sequence of any of SEQ ID NO: 1, 2, 4, or 5. These polypeptides and nucleic acids are related to S100 cytokine-like proteins, as disclosed herein.

Also included in the invention is a vector containing one or more of the nucleic acids described herein, and a cell containing the vectors or nucleic acids described herein. The invention is also directed to host cells transformed with a vector comprising any of the nucleic acid molecules described above.

In another aspect, the invention includes a pharmaceutical composition that includes an FCTRX nucleic acid and a pharmaceutically acceptable carrier or diluent.

In a further aspect, the invention includes a substantially purified FCTRX polypeptide, e.g., any of the FCTRX polypeptides encoded by an FCTRX nucleic acid, and fragments, homologs, analogs, and derivatives thereof. The invention also includes a pharmaceutical composition that includes an FCTRX polypeptide and a pharmaceutically acceptable carrier or diluent.

In a still further aspect, the invention provides an antibody that binds specifically to an FCTRX polypeptide. The antibody can be, e.g., a monoclonal or polyclonal antibody, and fragments, homologs, analogs, and derivatives thereof. The invention also includes a pharmaceutical composition including FCTRX antibody and a pharmaceutically acceptable carrier or diluent. The invention is also directed to isolated antibodies that bind to an epitope on a polypeptide encoded by any of the nucleic acid molecules described above. The invention also includes kits comprising any of the pharmaceutical compositions described above.

The invention further provides a method for producing an FCTRX polypeptide by providing a cell containing an FCTRX nucleic acid, e.g., a vector that includes an FCTRX nucleic acid, and culturing the cell under conditions sufficient to express the FCTRX polypeptide encoded by the nucleic acid. The expressed FCTRX polypeptide is then recovered from the cell. Preferably, the cell produces little or no endogenous FCTRX polypeptide. The cell can be, e.g., a prokaryotic cell or eukaryotic cell.

The invention is also directed to methods of identifying a FCTRX polypeptides or nucleic acids in a sample by contacting the sample with a compound that specifically binds to the polypeptide or nucleic acid, and detecting complex formation, if present.

The invention further provides methods of identifying a compound that modulates the activity of an FCTRX polypeptide by contacting FCTRX polypeptide with a compound and determining whether the FCTRX polypeptide activity is modified.

The invention is also directed to compounds that modulate FCTRX polypeptide activity identified by contacting an FCTRX polypeptide with the compound and determining whether the compound modifies activity of the FCTRX polypeptide, binds to the FCTRX polypeptide, or binds to a nucleic acid molecule encoding an FCTRX polypeptide.

In another aspect, the invention provides a method of determining the presence of or predisposition to an FCTRX-associated disorder in a subject. The method includes providing a sample from the subject and measuring the amount of FCTRX polypeptide in the subject sample. The amount of FCTRX polypeptide in the subject sample is then compared to the amount of FCTRX polypeptide in a control sample. An alteration in the amount of FCTRX polypeptide in the subject protein sample relative to the amount of FCTRX polypeptide in the control protein sample indicates the subject has pathology related to a dysfunction in the immune system, a tissue proliferation-associated condition, or a neurological disorder. A control sample is preferably taken from a matched individual, i.e., an individual of similar age, sex, or other general condition but who is not suspected of having a dysfunction in the immune system, a tissue proliferation-associated condition, or a neurological disorder. Alternatively, the control sample may be taken from the subject at a time when the subject is not suspected of having a dysfunction in the immune system, a tissue proliferation-associated condition, or a neurological disorder. In some embodiments, the FCTRX polypeptide is detected using an FCTRX antibody.

In a further aspect, the invention provides a method of determining the presence of, or predisposition to an FCTRX-associated disorder in a subject. The method includes providing a nucleic acid sample, e.g., RNA or DNA, or both, from the subject and measuring the amount of the FCTRX nucleic acid in the subject nucleic acid sample. The amount of FCTRX nucleic acid sample in the subject nucleic acid is then compared to the amount of FCTRX nucleic acid in a control sample. An alteration in the amount of FCTRX nucleic acid in the sample relative to the amount of FCTRX in the control sample indicates the subject has a dysfunction in the immune system, a tissue proliferation-associated condition, or a neurological disorder.

In a still further aspect, the invention provides a method of treating or preventing or delaying an FCTRX-associated disorder. The method includes administering to a subject in which such treatment or prevention or delay is desired an FCTRX nucleic acid, an FCTRX polypeptide, or an FCTRX antibody in an amount sufficient to treat, prevent, or delay an immune disorder, a tissue proliferation-associated disorder, or a neurological disorder in the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a ClustalW alignment of the carboxy 104 amino acids of the human polypeptide of SEQ ID NO:6 with known S100 cytokine proteins.

FIG. 2 is a ClustalW alignment of the human polypeptide of SEQ ID NO:6 and the murine ortholog of SEQ ID NO:3.

FIG. 3 is a Pfam analysis of the polypeptide (SEQ ID NO:38) encoded by human EST AA315020 (SEQ ID NO:4).

FIG. 4B shows an alignment of amino acids 28–128 of SEQ ID NO:3 with amino acids 1–101 of Acc. No. AY 007220, an S-100 type binding protein, and consensus sequence (SEQ ID NO:40).

FIG. 4C shows an alignment of amino acids 15–118 of SEQ ID NO:6 with amino acids 1–104 of Acc. No. AY007220, and consensus sequence (SEQ ID NO:49).

FIG. 4D shows an alignment of a region of the polypeptide of SEQ ID NO:3 with various calcium binding domains (SEQ ID NOs:41–44); the consensus sequence derived from the alignment is shown as SEQ ID NO:45.

FIG. 4E shows an alignment of a region of the polypeptide of SEQ ID NO:6 with various previously described calcium binding domains (SEQ ID NOs:41, 42, 44 and 46); the consensus derived from the alignment is shown as SEQ ID NO:47.

FIG. 7 is a CAP alignment and consensus of human assembly 6567721-3-frag (SEQ ID NO:5) compared to human EST AA315020 (SEQ ID NO:48; the complementary strand sequence of SEQ ID NO:4), and CuraGen assembly 65677221 (SEQ ID NO:37).

DETAILED DESCRIPTION OF THE INVENTION

Figure 4A:
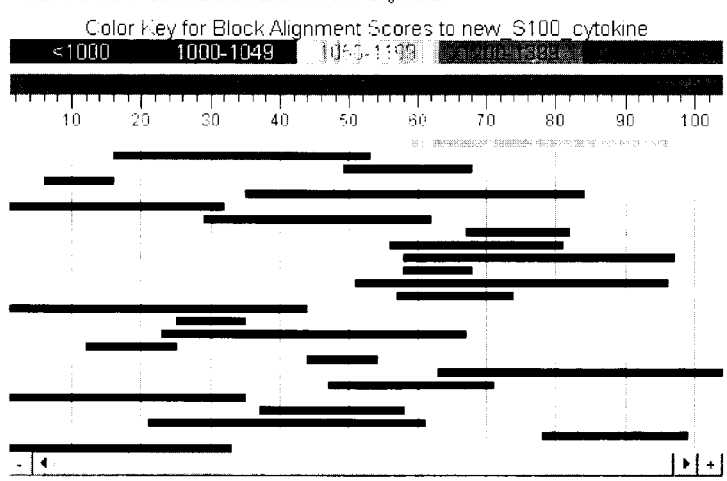
FIG. 4A is a BLOCKS protein domain analysis of the polypeptide of SEQ ID NO:6 with other calcium binding proteins (SEQ ID NOs:12–36).

The present invention discloses genes in the Wnt signaling pathway. Included in the invention is a nucleic acid expressed at different levels in murine mammary tumors that arise spontaneously in Wnt-1 transgenic mice relative to control tissues. The sequence of this differentially expressed sequence is shown in Table 1 (SEQ ID NO:1).

TABLE 1

Nucleotide sequence of murine clone 7971c.7.

(SEQ ID NO:1)
GAATTCAGTOATCTAGAGAGGGCCATTGAGACACTCATCAAGAACTTCCAT

AAATACTCTGTGGCGGCTAAAAAGGAAACACTGACCCCTGCTGAGCTTCGA

GACCTGGTTACCCAGCAGCTGCCACACCTCATGCCGAGCAACTGTGGGTTA

GAAGAGAAAATTGCCAACCTGGGCAACTGTAATGACTCGAAACTGGAGTTT

GGAAGCTT

The sequence shown in Table 1 was extended by assembly with other murine nucleic acid fragments. The resulting novel assembly, designated 7971c.7-r0s0-212.2-EXT (SEQ ID NO:2), is shown in Table 2.

TABLE 2

Nucleotide sequence of murine clone 7971c.7r0s0-212.2-EXT.

(SEQ ID NO:2)
TCAGGTGAGCTGGCTCCTCCATCCTGTCTCCCAGCTGCCAGCAGGTCTCCC

CCTCCTCTAGGTAGATCATGATCCATCAGCTCCTGTGGGGCAGGCTATAGG

ACAGACGACAAAACTCAACTCACAGAAGGAAGGACCAGTGTACCAGGAACG

ATGGGACAGTGTCGGTCAGCCAATGCTGAGGATGCCCAAGAATTCAGTGAT

GTAGAGAGGGCCATTGAGACACTCATCAAGAACTTCCATAAATACTCTGTG

GCGGGTAAAAAGGAAACACTGACCCCTGCTGAGCTTCGAGACCTGGTTACC

CAGCAGCTGCCACACCTCATGCCGAGCAACTGTGGGTTAGAAGAGAAAATT

GCCAACCTGGGCAACTGTAATGACTCGAAACTGGAGTTTGGAAGCTTCTGG

GAGTTGATTGGAGAAGCAGCCAAGAGTGTGAAGATGGACAGGCCTGTTACT

CGGAGCTGAGGACTTCTACTTGGAACTTGTTGGGGGTGTTGGGGATAGGG

AGTTTTAGAGGCACTGGAAATAAAACCCTCAATGCCCACCACCCCCTTCCC

CAGCCTGCACCTCTCCTCATTGCTGCAATGTTCACGTTCAGGACAGGCTTC

CCTGTGGCCTCCATGGAGCTCCTGGGTCCAGAAGTCCTCATCTCAAGGGAG

CTCAGGGGGTGGGTTGGGGCTGGAGAGGATATGCAGGGATCCTGGAAGGGT

AAGGGCCAAGCAATTTGGTAGTAGGGGAAGGGCAGAAAGGAACTGGGTTAT

GGAAGTGATCCAAAGAGCAGGGATGGGAATCTGGCTGCATATTTGGTCCTG

AAAAGGGTGTCTGAGAACCTACCCCCTTCTAATCTTGTCCCACCTAAACTG

TAGTTGTCTGCCCTGTGCTATCCTTGCTGCTTCCAGCTCTGCCCCATCCTC

CTTCCAGTGTCTGTTCCTGAGTAGGGGCAGGGGAAATAGGAGCAGAGTTGC

AAAAGAGGCTGAGGAGGGCATGACTTCATCACTTTGGGGTGAGAGGACCAG

CTAGATGCTTGGGCATTTATGGTAGTTATTTTATATCATTTGATTAATAAA

AATATTGGAAAATGTAAAGAAAAAAAAGAAAAAAACATGGGGCCGAAACC

TTATCCCCCTTGAGTAGGGTGATATTTTGCGTGTGCAATGGGCGGCCTGTT

TTCGAGAGGCGGTGACATGGGGAAAACATGGGGGTGTACCAAACCTTAACC

GCCTTTTAGGGGAAACACCCCTTTTGCCGCAAGTGGGTTAATAACGAAGA

AGCCCGGCCGGATTGCCCTTCACAAGAGTCTCCCGCGGTAGATGCGGATGG

GACAGCCCCCTTCGGCGGCGTTTAGAGCGGCGTGTGTGTGGTTTCTACGCG

AATAGGGATAAATATTGTGGCGGCGCCGAGGGAGTGTGTGTGTTGCGCGCC

TGCTTCTGTGGAGGTGGTGTGTCCCAAAAACTAAAAGGGCCCTTTTGTGCG

CGTTAGTTTGCTCTAGCAGAGTCCGCTGCACATATTTTGGTGGGCGTGTCC

GTGCCGCCCGNGGTGGTGCTTGTTGCTGGCGTGGCGTGGGGTGGGTGTGGT

TGCGGGGGTGGTCGTGTTGGGTGTGTGCGTGCGCGCGGGGGCCGTGTGTGT

GTGTGGTTGCATGATAAGGTTAGAGTGAGTGAGAGCGG

The murine sequence shown in Table 2 includes an open reading frame ("ORF") from nucleotide 73 to nucleotide 465. The beginning of this ORF is indicated in bold in Table 2. The polypeptide encoded by this ORF is shown in Table 3 (SEQ ID NO:3).

TABLE 3

Translation product of murine clone 7971c.7r0s0-212.2-EXT.

(SEQ ID NO:3)
SISSCGAGYRTDDKTQLTEGRTSVPGTMGQCRSANAEDAQEFSDVERAIET

LIKNFHKYSVAGKKETLTPAELRDLVTQQLPHLMPSNCGLEEKIANLGNCN

DSKLEFGSFWELIGEAAKSVKMERPVTRS

The murine sequence shown in Table 1 is related to human EST AA315020. This EST originates from human cells forming a metastatic tumor when implanted in mice. The sequence of this EST is shown in Table 4 (SEQ ID NO:4).

TABLE 4

Nucleotide sequence of human EST AA3 15020.

(SEQ ID NO:4)
ATAGGACAACAGAACTCTCACCAAAGGACCAGACACAGTGAGCACCATGGG

ACAGTGTCGGTCAGCCAACGCAGAGGATGCTCAGGAATTCAGTGATGTGGA

GAGGGCCATTGAGACCCTCATCAAGAACTTTCACCAGTACTCCGTGGAGGG

TGGGAAGGAGACGCTGACCCCTTCTGAGCTACGGGACCTGGTCACCCAGCA

GCTGCCCCATCTCATGCCGAGCAACTNTGGCCTGGAAGAGAAAATTGCCAA

CCTGGGCAGCTGGAATCACTCTAAACTGGAGTTCAGGAGTTTCTGGGAGCT

GATTGGAGAAGCGGCCAAGAGTGTGAAGCTNGAGAGGACTGTCCGGGGGCA

A consensus sequence (SEQ ID NO:5) of 294 bp was assembled as described in Example 2. The consensus sequence shown in Table 5 encompasses and extends human EST AA315020 (SEQ ID NO:4).

TABLE 5

Human Consensus Sequence 65677221-3-frag (SEQ ID NO:5)

GAATTCCAGAGGGAGTTCTCAGTGC-
CCCCGGACAGGCCTCTCCAGCTTCAC

ACTCTTGCCCGCTTCTCCAATCAGCTC-
CCAGAAACTCCTGAACTCCAGTTT

AGAGTCATTGCAGCTGCCCAGGTTG-
GCAATTTTCTCTTCCAGGCCACAGTT

GCTCGGCATGAGATGGGGCAGCT-
GCTGGGTGACCAGGTCCCGTAGCTCAGA

AGGGGTCAGCGTCTCCTTCCCACCCTC-
CACGGAGTACTGGTGAAAGTTCTT

GATGAGGGTCTCAATGGCCCTCTCCA-
CATCACTGAATTCCTGAGCATCCTC

TGCGTTGGCTGACCGACACTGTCCCATG-
GTGCTCACTGTGTCTGGTCCTTT

GGTGAGAGTTCTGTTGTCCTAT

The nucleotide sequence shown in Table 5 includes an ORF that encodes a translation product having the sequence shown in Table 6 (SEQ ID NO:6).

TABLE 6

Predicted translation of 65677221-3-frag.

(SEQ ID NO:6)
DNRTLTKGPDTVSTMGQCRSANAEDAQEFSDVERAIETLIKNFHQYSVEGG

KETLTPSELRDLVTQQLPHLMPSNCGLEEKIANLGSCNDSKLEFRSFWELI

GEAAKSVKLERPVRGH

The polypeptides whose sequences are shown in Table 3 and Table 6 have a high degree of similarity with the S100 family of proteins. FIG. 1 demonstrates this similarity for the human sequence shown in Table 6. The sequence identified as "W27152" in FIG. 1 is disclosed as a "chemotactic cytokine II CCII polypeptide" in PCT publication WO97/34013, and the polypeptide designated "G491246" is a Macrophage Migration Inhibition Factor (MRP-14).

The mouse and human amino acid sequences of Table 3 and Table 6 are shown aligned in FIG. 2. This alignment reveals that these two sequences are sufficiently similar such that they can be considered to be orthologs. The region of similarity between the human and the mouse proteins begins just before this first Met of the human sequence and ends just before the stop codon. In addition, the codon encoding the first Met is located near a Kozak consensus sequence. Analysis by the Pfam algorithm that identifies relates protein families indicates that the polypeptide encoded by the human EST AA315020 (SEQ ID NO:4) is related to the S100 family (FIG. 3).

Moreover, analysis by the BLOCKS program (see FIG. 4A) shows the two conserved calcium binding regions separated by 8 amino acids, which is characteristic of S100 proteins (Kligman, 1988 Trends Biochem. Sci. 13:437). Sequences shown in FIG. 4A are identified in Table 11.

TABLE 11

| SEQ ID NO: | Molecule | SEQ ID NO: | Molecule |
| --- | --- | --- | --- |
| 12 | 3-100/ICaBP type calcium binding protein | 25 | Glypicans protein |
| 13 | 3-100/ICaBP type calcium binding protein | 26 | Membrane attack complex component/perforin |
| 14 | Bacterial type II secretion system protein F | 27 | Urease nickel ligands protein |
| 15 | Ubiquitin carboxyl-terminal hydrolases family | 28 | Phosphoglycerate mutase family phosphohistidine |
| 16 | Bacterial chemotaxis sensory transducers protein | 29 | Ribosomal protein L23 protein |
| 17 | Phosphoenolpyruvate carboxykinase (ATP) protein | 30 | 2'-5'-oligoadenylate synthetase protein |
| 18 | Prokaryotic-type carbonic anhydrases protein | 31 | Formate and nitrite transporter protein |
| 19 | Ergosterol biosynthesis ERG4/ERG24 family protein | 32 | Glycoprotein hormones β chain protein |
| 20 | Lysosome-associated membrane glycoproteins duplicated domains protein | 33 | Vinculin family talin-binding region protein |
| 21 | Phosphofructokinase proteins | 34 | β-lactamase class B protein |
| 22 | pH domain proteins profile | 35 | Heat shock hsp20 protein family profile |
| 23 | Myotoxins protein | 36 | Hydroxymethylglutaryl-coenzyme A lyase protein |
| 24 | Phosphatidylinositol-specific phospholipase X | | |

FIGS. 4B–4E show comparisons of portions of the amino acid sequences shown in Table 3 (SEQ ID NO:3) and Table 6 (SEQ ID NO:6) to S-100-type calcium binding proteins. FIG. 4B shows an alignment of amino acids 28–128 of SEQ ID NO:3 with amino acids 1–101 of Acc. No. AY007220 (SEQ ID NO:39) an S-100 type calcium binding protein. Identical or conserved amino acid residues are indicated in black shading. These residues may be required to preserve structural or functional properties of the protein. Amino acids shaded in gray can be mutated to a residue with comparable steric and/or chemical properties without altering protein structure or function, e.g., L to V, I or M. Non-highlighted amino acid can potentially be mutated to a much broader extent without altering structure or function.

FIG. 4C shows an alignment of amino acids 15–118 of SEQ ID NO:6 with amino acids 1–104 of Acc. No. AY007220. Shading is as explained for FIG. 4B.

FIGS. 4B and 4C demonstrate that the polypeptides shown in Tables 3 and 6 included extensive regions identical or conserved with the amino acid sequence of Acc. No. AY0077220 (SEQ ID NO:39); amino acids 15–118 of SEQ ID NO:6 are shown in FIGS. 4B and 4C; the consensus sequence derived from these alignments is given as SEQ ID NO:40.

The polypeptide sequences shown in Tables 3 and 6 include sequences highly homologous to previously-described S-100/ICaBP-type calcium binding domains. These calcium binding domains are discussed in Sastry et al., Structure 6:223–31, 1998. Proteins containing these domains are implicated in cell growth and division. In addition, expression of these proteins is reported to be deregulated in transformed cells. For example, high levels of these proteins have been reported in some breast cancers.

FIG. 4D shows an alignment of a region of the polypeptide of Table 3 (amino acids 46 to 85 SEQ ID NO:3) with various calcium binding domains (SEQ ID NOs:41 (gi/4139958/pbd/1MHO), 42 (Protein MRP-126), 43 (ICTACALCIN) and 44 (CALGRANULIN B). The consensus sequence is given in SEQ ID NO:4. FIG. 4E shows an alignment of a region of the polypeptide of Table 6 (amino acids 33 to 72 of SEQ ID NO:6) with various previously described calcium binding domains (SEQ ID NOs:41 (gi/4139958/pdb/1MHO), 42 (Protein MRP-126), 44 (CALGRANULIN B and 46 (CALGRANULIN B). The consensus sequence is given in SEQ ID NO:47.

Figure 5:
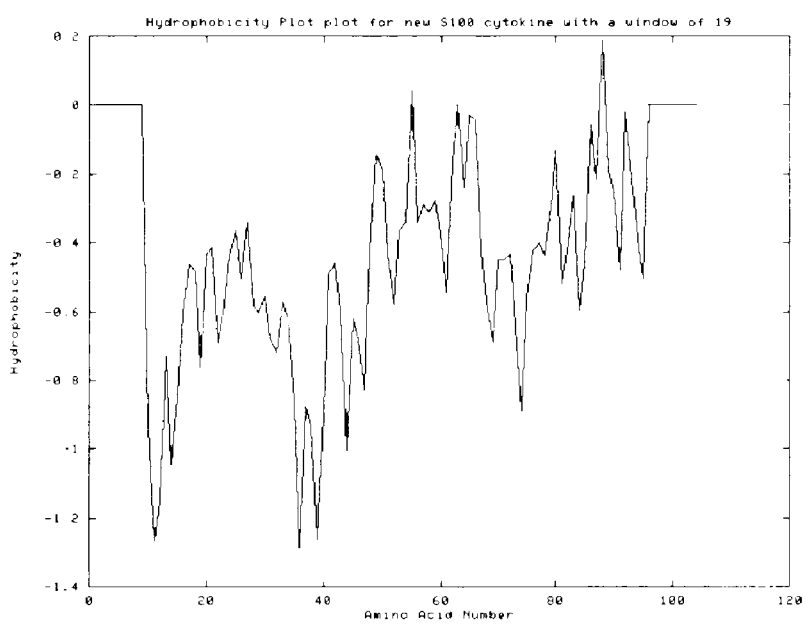
FIG. 5 is a hydrophobicity plot of the polypeptide of SEQ ID NO:6.

The hydrophobicity plot of this polypeptide, shown in FIG. 5, suggests that its amino acid sequence is highly hydrophilic, so that it is disposed neither toward membrane localization nor toward secretion. This is confirmed by PSORT analysis, which predicts that the polypeptide localizes in the cytoplasm. Cytoplasmic localization is another characteristic of S100 proteins (Dale et al. 1983 Eur. J. Biochem. 134:1–6). S100 proteins fall into a category of proteins that have extracellular function but are released, rather than being secreted.

It is expected that the serum concentration of a S100 cytokine according to the invention (e.g., a polypeptide having the amino acid sequence of SEQ ID NO:3 or SEQ ID NO:6) can be used as a marker for the clinical predictive value for metastatic tumors. Notably, the mouse gene fragment disclosed in Table 1 (SEQ ID NO:1) was originally identified in the tumors of Wnt-1 transgenic mice. In addition, two of the human fragments used to produce the sequence shown in Table 5 (SEQ ID NO:5) were isolated from tumors. In addition, as is shown in Example 3, the sequence shown in Table 5 (SEQ ID NO:5) is highly expressed in several tumor cell lines, especially in colon cancer, breast cancer and ovarian cancer. For all these reasons, the nucleic acids and their gene products identified herein are useful as diagnostic markers for such cancers, and as targets for the treatment of cancer in a subject. The targeting may especially be carried out by generating antibodies that specifically bind a protein encoded by SEQ ID NO:5, and administering such antibodies to a subject suffering from a cancer such as colon cancer, breast cancer or ovarian cancer. These antibodies will likewise serve as diagnostic tools useful in detecting the presence or amount of the proteins disclosed herein.

A FCTRX polypeptide according to the invention includes a polypeptide including the amino acid sequences of SEQ ID NO:3 or SEQ ID NO:6, as well as homologs, and variants as described herein. A FCTRX nucleic acid according to the invention includes the nucleic acids shown in SEQ ID NO:1, 2, 4, or 5 as well as homologs and variants disclosed herein.

S100 Cytokine Polypeptides

The FCTRX polypeptides are homologous to members of the S100 cytokine family. The S100 group of proteins are calcium-binding molecules with cytokine and chemokine activity. For example, the murine protein S100A8 is a potent chemoattractant for neutrophils and monocytes in vivo and in vitro (Xu K and Geczy C L, J Immunol 2000 May 1:164(9):4916–23).

The S100 family of Ca2+-binding proteins that contain EF-hand Ca+2 binding motifs includes 19 members that are differentially expressed in a large number of cell types. Members of this protein family have been implicated in the Ca2+-dependent regulation of intracellular activities as diverse as protein phosphorylation, enzyme activities, cell proliferation (including neoplastic transformation) and differentiation, cytoskeleton and membrane remodeling, the structural organization of membranes, intracellular Ca2+ homeostasis, inflammation, and in protection from oxidative cell damage. S100 proteins have also been implicated in Zn2+- or Cu2-dependent activities. Some S100 members are released or secreted into the extracellular space and exert trophic or toxic effects (depending on their concentration). Family members can also act as chemoattractants for leukocytes, modulate cell proliferation, or regulate macrophage activation (Donato, 1999 Biochim Biophys Acta 8:191–231). The serum concentration of S100 has been shown to have clinical predictive value for metastatic tumors.

S100 family members have also been reported to interact with each other. For example, recombinantly expressed murine S100A9 has been reported to interact in vitro with murine and human S100A8 (Nacken et al., Eur J Biochem 2000 January:267(2):560–5). Both murine S100A9 and its dimerization partner mS100A8 are expressed at the onset of granulocyte-colony stimulating factor induced myeloid differentiation. Substantial amounts of this complex are constitutively secreted by granulocytic 32D cells into the medium. It has also been suggested that the human and murine S100A9 may share a higher degree of functional homology than of sequence similarity (Nacken et al., 2000).

Two S100 family proteins, S100B and S100A1, activate RAGE, (the receptor for an advanced glycation end product (AGE)) occurring in diabetes in concert with amphoterin. This interaction is reported to induce neurite outgrowth and activation of transcription factor NF-kappaB. Amphoterin is a protein that enhances process extension and migration in embryonic neurons and in tumors cells through binding to RAGE, a multiligand transmembrane receptor. Furthermore, activation of RAGE by amphoterin and S100B promotes cell survival through increased expression of the anti-apoptotic protein Bcl-2. Higher concentrations of S100B induce apoptosis in an oxidant-dependent manner. Activation of RAGE by multiple ligands may promote trophic effects, whereas hyperactivation of RAGE signaling pathways promotes apoptosis.

Specific staining of WHO grade II and III astrocytic tumors with S100 calcium-binding proteins has been used to characterizes distinct clinical entities in both WHO grade II and III astrocytic tumors. The grade II and III astrocytic tumors lead to different clinical outcomes (Camby et al., Neuropathol Appl Neurobiol 2000 February;26(1):76–90). The level of cell proliferation (determined by means of both anti-proliferating cell nuclear antigen and anti-MIB-1 antibodies differed significantly between astrocytomas and anaplastic astrocytomas. In sharp contrast, the levels of expression of the S100A3 and S100A5 proteins differed markedly in the solid tumor tissue in relation to the astrocytic tumor types and grades. In addition, while the levels of expression of S100A6 did not change in the astrocytic tumor tissue in relation to histopathological grade, the levels of expression of S100A6 (but not those of S100A3 and S100A5) differed markedly in the blood vessel walls according to whether these vessels originated from low- or high-grade astrocytic tumors. Thus S100 proteins have highly specific expression levels and degrees of association with varying cell types and tissues.

Noncancerous CNS pathologies are also related to S100 proteins. Homozygous APPV717F transgenic mice overexpress a human beta-amyloid precursor protein (betaAPP) minigene encoding a familial Alzheimer's disease mutation. These mice develop Alzheimer-type neuritic beta-amyloid plaques surrounded by astrocytes. S100beta is an astrocyte-derived cytokine that promotes neurite growth and promotes excessive expression of betaAPP. S100beta overexpression in Alzheimer's disease correlates with the proliferation of betaAPP-immunoreactive neurites in beta-amyloid plaques. Age-related increases in tissue levels of both betaAPP and S100beta mRNA have been reported in transgenic mice (Sheng et al., J Neurochem 2000 January;74(1):295–301). Accelerated age-related overexpression of S100beta may interact with age-associated overexpression of mutant betaAPP in transgenic mice to promote development of Alzheimer-like neuropathological changes.

Levels of S100 beta in serum is also a significant prognostic marker for malignant melanoma (Djukanovic etl al., Anticancer Res 2000 May–June:20(3B):2203–7). In 53 melanoma patients a direct correlation of S100 values and clinical course could be observed (81.5%). S100 beta levels were incorrectly elevated in 5 out of 25 sera, giving "false positive" results (20%) and in 8 out of 40 sera were not elevated despite the detection of metastases giving "false negative" results (20%).

FCTRX Nucleic Acids

One aspect of the invention pertains to isolated nucleic acid molecules that encode FCTRX proteins or biologically active portions thereof, as well as nucleic acid fragments sufficient for use as hybridization probes to identify FCTRX-encoding nucleic acids (e.g., FCTRX mRNA) and fragments for use as PCR primers for the amplification or mutation of FCTRX nucleic acid molecules.

As used herein, the term "nucleic acid molecule" is intended to include DNA molecules (e.g., cDNA or genomic DNA). RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

An "isolated" nucleic acid molecule is one that is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated FCTRX nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

In some embodiments, the FCTRX nucleic acids encode a mature form a FCTRX polypeptide. As used herein, the term a "mature" form of a polypeptide or protein is the product of a naturally occurring polypeptide or precursor form of FCTRX-protein. The naturally occurring polypeptide, precursor or FCTRX-protein includes, by way of non-limiting example, the full length gene product, encoded by the corresponding gene. Alternatively, it may be defined as the polypeptide, precursor or FCTRX-protein encoded by an open reading frame described herein. The product "mature" form arises, again by way of non-limiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristylation, or phosphorylation. In general, a mature polypeptide or protein may result from the operation of only one of these processes, or a combination of any of them.

A nucleic acid molecule of the present invention, e.g., a nucleic acid molecule having the nucleotide sequence of SEQ ID NO:1, 2, 4, or 5, or a complement of any of these nucleotide sequences, can be isolated using standard molecular biology techniques and the sequence information provided herein. Using all or a portion of the nucleic acid sequences of SEQ ID NO:1, 2, 4, or 5 as a hybridization probe, FCTRX molecules can be isolated using standard hybridization and cloning techniques (e.g., as described in Sambrook et al., eds., MOLECULAR CLONING: A LABORATORY MANUAL 2$^{nd}$ Ed., Cold Spring Harbor Laboratory Press, Cold Spring Harbor, NY, 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to FCTRX nucleotide sequences can be prepared by standard synthetic techniques, e.g., using an automated DNA synthesizer.

In another embodiment, an isolated nucleic acid molecule of the invention comprises a nucleic acid molecule that is a complement of the nucleotide sequence shown in SEQ ID NO:1, 2, 4, or 5. In another embodiment, an isolated nucleic acid molecule of the invention comprises a nucleic acid molecule that is a complement of the nucleotide sequence shown in SEQ ID NO:1, 2, 4, or 5, or a portion of this nucleotide sequence. A nucleic acid molecule that is complementary to the nucleotide sequence shown in SEQ ID NO:1, 2, 4, or 5 is one that is sufficiently complementary to the nucleotide sequence shown in SEQ ID NO:1, 2, 4, or 5 that it can hydrogen bond with little or no mismatches to the nucleotide sequence shown in SEQ ID NO:1, 2, 4, or 5 thereby forming a stable duplex.

Moreover, the nucleic acid molecule of the invention can comprise only a portion of the nucleic acid sequence of SEQ ID NO:1, 2, 4, or 5, e.g., a fragment that can be used as a probe or primer or a fragment encoding a biologically active portion of an FCTRX. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 30%, 50%, 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

The nucleotide sequence determined from the cloning of a human FCTRX gene allows for the generation of probes and primers designed for use in identifying and/or cloning FCTRX homologues in other cell types, e.g. from other tissues, as well as FCTRX homologues from other mammals. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NO:1, 2, 4, or 5 or an anti-sense strand nucleotide sequence of SEQ ID NO:1, 2, 4, or 5 or of a naturally occurring mutant of one or more of these sequences.

Probes based on the human FCTRX nucleotide sequence can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress an FCTRX protein, such as by measuring a level of an FCTRX-encoding nucleic acid in a sample of cells from a subject e.g., detecting FCTRX mRNA levels or determining whether a genomic FCTRX gene has been mutated or deleted.

"A polypeptide having a biologically active portion of FCTRX" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of FCTRX" can be prepared by isolating a portion of SEQ ID NO:1, 2, 4, or 5 that encodes a polypeptide having a FCTRX biological activity (the biological activities of the FCTRX proteins are described above), expressing the encoded portion of FCTRX protein (e.g., by recombinant expression in vitro) and assessing the activity of the encoded portion of FCTRX.

FCTRX Variants

The invention further encompasses nucleic acid molecules that differ from the nucleotide sequence shown in SEQ ID NO:1, 2, 4, or 5 due to degeneracy of the genetic code and thus encode the same FCTRX protein as that encoded by the nucleotide sequence shown in SEQ ID NO:1, 2, 4, or 5. In another embodiment, an isolated nucleic acid molecule of the invention has a nucleotide sequence encoding a protein having an amino acid sequence shown in SEQ ID NO: 3 or 6.

In addition to the human FCTRX nucleotide sequence shown in SEQ ID NO:1, 2, 4, or 5 it will be appreciated by those skilled in the art that DNA sequence polymorphisms that lead to changes in the amino acid sequences of FCTRX may exist within a population (e.g., the human population). Such genetic polymorphism in the FCTRX gene may exist among individuals within a population due to natural allelic variation. As used herein, the terms "gene" and "recombinant gene" refer to nucleic acid molecules comprising an open reading frame encoding an FCTRX protein, preferably a mammalian FCTRX protein. Such natural allelic variations can typically result in 1–5% variance in the nucleotide sequence of the FCTRX gene. Any and all such nucleotide variations and resulting amino acid polymorphisms in FCTRX that are the result of natural allelic variation and that do not alter the functional activity of FCTRX are intended to be within the scope of the invention.

Moreover, nucleic acid molecules encoding FCTRX proteins from other species, and thus that have a nucleotide sequence that differs from the human sequence of SEQ ID NO:1, 2, 4, or 5 are intended to be within the scope of the invention. Nucleic acid molecules corresponding to natural allelic variants and homologues of the FCTRX cDNAs of the invention can be isolated based on their homology to the human FCTRX nucleic acids disclosed herein using the human cDNAs, or a portion thereof, as a hybridization probe according to standard hybridization techniques under stringent hybridization conditions. For example, a soluble human FCTRX cDNA can be isolated based on its homology to human membrane-bound FCTRX cDNA. Likewise, a membrane-bound human FCTRX cDNA can be isolated based on its homology to soluble human FCTRX cDNA.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1, 2, 4, or 5. In another embodiment, the nucleic acid is at least 10, 25, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding FCTRX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6× SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2× SSC, 0.01% BSA at 50° C. An isolated nucleic acid molecule of the invention that hybridizes under stringent conditions to the sequence of SEQ ID NO:1, 2, 4, or 5 corresponds to a naturally-occurring nucleic acid molecule. As used herein, a "naturally-occurring" nucleic acid molecules refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, 2, 4, or 5, or fragments, analogs or derivatives thereof, under conditions of moderate stringency is provided. A non-limiting example of moderate stringency hybridization conditions are hybridization in 6× SSC, 5× Denhardt's solution, 0.5% SDS and 100 mg/ml denatured salmon sperm DNA at 55° C., followed by one or more washes in 1× SSC, 0.1% SDS at 37° C. Other conditions of moderate stringency that may be used are well-known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, 2, 4, or 5 or fragments, analogs or derivatives thereof, under conditions of low stringency, is provided. A non-limiting example of low stringency hybridization conditions are hybridization in 35% formamide, 5× SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2× SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789–6792.

Conservative Mutations

In addition to naturally-occurring allelic variants of the FCTRX sequence that may exist in the population, the skilled artisan will further appreciate that changes can be introduced by mutation into the nucleotide sequence of SEQ ID NO:1, 2, 4, or 5 thereby leading to changes in the amino acid sequence of the encoded FCTRX protein, without altering the functional ability of the FCTRX protein. For example, nucleotide substitutions leading to amino acid substitutions at "non-essential" amino acid residues can be made in the sequence of SEQ ID NO:1, 2, 4, or 5. A "non-essential" amino acid residue is a residue that can be altered from the wild-type sequence of FCTRX without altering the biological activity, whereas an "essential" amino acid residue is required for biological activity. For example, amino acid residues that are conserved among the FCTRX proteins of the present invention, are predicted to be particularly unamenable to alteration.

Another aspect of the invention pertains to nucleic acid molecules encoding FCTRX proteins that contain changes in amino acid residues that are not essential for activity. Such FCTRX proteins differ in amino acid sequence from SEQ ID NO:3 or 6, yet retain biological activity. In one embodiment, the isolated nucleic acid molecule comprises a nucleotide sequence encoding a protein, wherein the protein comprises an amino acid sequence at least about 45% homologous to the amino acid sequence of SEQ ID NO:3 or 6. Preferably, the protein encoded by the nucleic acid molecule is at least about 60% homologous to SEQ ID NO:3 or 6, more preferably at least about 70% homologous to SEQ ID NO:3 or 6, still more preferably at least about 80% homologous to SEQ ID NO:3 or 6, even more preferably at least about 90% homologous to SEQ ID NO:3 or 6, and most preferably at least about 95% homologous to SEQ ID NO:3 or 6.

An isolated nucleic acid molecule encoding a FCTRX protein homologous to the protein of SEQ ID NO:3 or 6 can be created by introducing one or more nucleotide substitutions, additions or deletions into the nucleotide sequence of SEQ ID NO:1, 2, 4, or 5 such that one or more amino acid substitutions, additions or deletions are introduced into the encoded protein.

Mutations can be introduced into SEQ ID NO:1, 2, 4, or 5 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in FCTRX is replaced with another amino acid residue from the same side chain family. Alternatively, in another embodiment, mutations can be introduced randomly along all or part of a FCTRX coding sequence, such as by saturation mutagenesis, and the resultant mutants can be screened for FCTRX biological activity to identify mutants that retain activity. Following mutagenesis of SEQ ID NO:1, 2, 4, or 5, the encoded protein can be expressed by any recombinant technology known in the art and the activity of the protein can be determined.

In one embodiment, a mutant FCTRX protein can be assayed for (1) the ability to form protein:protein interactions with other FCTRX proteins, other cell-surface proteins, or biologically active portions thereof, (2) complex formation between a mutant FCTRX protein and a FCTRX ligand; (3) the ability of a mutant FCTRX protein to bind to an intracellular target protein or biologically active portion thereof; (e.g. avidin proteins).

Antisense

Another aspect of the invention pertains to isolated antisense nucleic acid molecules that are hybridizable to or complementary to the nucleic acid molecule comprising the nucleotide sequence of SEQ ID NO:1, 2, 4, or 5 or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire FCTRX coding strand, or to only a portion thereof. Nucleic acid molecules encoding fragments, homologs, derivatives and analogs of an FCTRX protein of SEQ ID NO:3 or 6, or antisense nucleic acids complementary to an FCTRX nucleic acid sequence of SEQ ID NO:1, 2, 4, or 5 are additionally provided.

In one embodiment, an antisense nucleic acid molecule is antisense to a "coding region" of the coding strand of a nucleotide sequence encoding FCTRX. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding FCTRX. The term "noncoding region" refers to 5' and 3' sequences which flank the coding region that are not translated into amino acids (i.e., also referred to as 5' and 3' untranslated regions).

Given the coding strand sequences encoding FCTRX disclosed herein (e.g., SEQ ID NO:1, 2, 4, or 5), antisense nucleic acids of the invention can be designed according to the rules of Watson and Crick or Hoogsteen base pairing. The antisense nucleic acid molecule can be complementary to the entire coding region of FCTRX mRNA, but more preferably is an oligonucleotide that is antisense to only a portion of the coding or noncoding region of FCTRX mRNA. For example, the antisense oligonucleotide can be complementary to the region surrounding the translation start site of FCTRX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a FCTRX protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual-β-units, the strands run parallel to each other (Gaultier et al. (1987) *Nucleic Acids Res* 15:6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave FCTRX mRNA transcripts to thereby inhibit translation of FCTRX mRNA. A ribozyme having specificity for an FCTRX-encoding nucleic acid can be designed based upon the nucleotide sequence of an FCTRX cDNA disclosed herein (i.e., SEQ ID NO:1, 2, 4, or 5). For example, a derivative of a Tetrahymena L-19 IVS RNA can be constructed in which the nucleotide sequence of the active site is complementary to the nucleotide sequence to be cleaved in a FCTRX-encoding mRNA. See, e.g., Cech et al. U.S. Pat. No. 4,987,071; and Cech et al. U.S. Pat. No. 5,116,742. Alternatively, FCTRX mRNA can be used to select a catalytic RNA having a specific ribonuclease activity from a pool of RNA molecules. See, e.g., Bartel et al., (1993) *Science* 261:1411–1418.

Alternatively, FCTRX gene expression can be inhibited by targeting nucleotide sequences complementary to the regulatory region of the FCTRX (e.g., the FCTRX promoter and/or enhancers) to form triple helical structures that prevent transcription of the FCTRX gene in target cells. See generally, Helene, (1991) *Anticancer Drug Des.* 6: 569–84; Helene, et al. (1992) *Ann. N.Y. Acad. Sci.* 660:27–36; and Maher (1992) *Bioassays* 14: 807–15.

In various embodiments, the nucleic acids of FCTRX can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of FCTRX can be used in therapeutic and diagnostic applications. For example, PNAs can be used as antisense or antigene agents for sequence-specific modulation of gene expression by, e.g., inducing transcription or translation arrest or inhibiting replication. PNAs of FCTRX can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of FCTRX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of FCTRX can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

FCTRX Proteins

One aspect of the invention pertains to isolated FCTRX proteins, and biologically active portions thereof, or derivatives, fragments, analogs or homologs thereof. Also provided are polypeptide fragments suitable for use as immunogens to raise anti-FCTRX antibodies. In one embodiment, native FCTRX proteins can be isolated from cells or tissue sources by an appropriate purification scheme using standard protein purification techniques. In another embodiment, FCTRX proteins are produced by recombinant DNA techniques. Alternative to recombinant expression, a FCTRX protein or polypeptide can be synthesized chemically using standard peptide synthesis techniques.

An "isolated" or "purified" protein or biologically active portion thereof is substantially free of cellular material or other contaminating proteins from the cell or tissue source from which the FCTRX protein is derived, or substantially free from chemical precursors or other chemicals when chemically synthesized. The language "substantially free of cellular material" includes preparations of FCTRX protein in which the protein is separated from cellular components of the cells from which it is isolated or recombinantly produced. In one embodiment, the language "substantially free of cellular material" includes preparations of FCTRX protein having less than about 30% (by dry weight) of non-FCTRX protein (also referred to herein as a "contaminating protein"), more preferably less than about 20% of non-FCTRX protein, still more preferably less than about 10% of non-FCTRX protein, and most preferably less than about 5% non-FCTRX protein. When the FCTRX protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of FCTRX protein in which the protein is separated from chemical precursors or other chemicals that are involved in the synthesis of the protein. In one embodiment, the language "substantially free of chemical precursors or other chemicals" includes preparation of FCTRX protein having less than about 30% (by dry weight) of chemical precursors or non-FCTRX chemicals, more preferably less than about 20% chemical precursors or non-FCTRX chemicals, still more preferably less than about 10% chemical precursors or non-FCTRX chemicals, and most preferably less than about 5% chemical precursors or non-FCTRX chemicals.

Biologically active portions of an FCTRX protein include peptides comprising amino acid sequences sufficiently homologous to or derived from the amino acid sequence of the FCTRX protein, e.g., the amino acid sequence shown in SEQ ID NO:3 or 6, that include fewer amino acids than the full length FCTRX proteins, and exhibit at least one activity of a FCTRX protein. Typically, biologically active portions comprise a domain or motif with at least one activity of the FCTRX protein. A biologically active portion of an FCTRX protein can be a polypeptide which is, for example, 10, 25, 50, 100 or more amino acids in length.

Moreover, other biologically active portions, in which other regions of the protein are deleted, can be peppered by recombinant techniques and evaluated for one or more of the functional activities of a native FCTRX protein.

In an embodiment, the FCTRX protein has an amino acid sequence shown in SEQ ID NO:3 or 6. In other embodiments, the FCTRX protein is substantially homologous to SEQ ID NO:3 or 6, and retains the functional activity of the protein of SEQ ID NO:3 or 6, yet differs in amino acid sequence due to natural allelic variation or mutagenesis, as described in detail below. Accordingly, in another embodiment, the FCTRX protein is a protein that comprises an amino acid sequence at least about 45% homologous to the amino acid sequence of SEQ ID NO:3 or 6 and retains the functional activity of the FCTRX proteins of SEQ ID NO:3 or 6.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1, 2, 4, or 5.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides FCTRX chimeric or fusion proteins. As used herein, an FCTRX "chimeric protein" or "fusion protein" comprises an FCTRX polypeptide operatively linked to a non-FCTRX polypeptide. An "FCTRX polypeptide" refers to a polypeptide having an amino acid sequence corresponding to FCTRX, whereas a "non-FCTRX polypeptide" refers to a polypeptide having an amino acid sequence corresponding to a protein that is not substantially homologous to the FCTRX protein, e.g., a protein that is different from the FCTRX protein and that is derived from the same or a different organism. Within an FCTRX fusion protein the FCTRX polypeptide can correspond to all or a portion of an FCTRX protein. In one embodiment, an FCTRX fusion protein comprises at least one biologically active portion of an FCTRX protein. In another embodiment, an FCTRX fusion protein comprises at least two biologically active portions of an FCTRX protein. In yet another embodiment, an FCTRX fusion protein comprises at least three biologically active portions of an FCTRX protein. Within the fusion protein, the term "operatively linked" is intended to indicate that the FCTRX polypeptide and the non-FCTRX polypeptide are fused in-frame to each other. The non-FCTRX polypeptide can be fused to the N-terminus or C-terminus of the FCTRX polypeptide.

In yet another embodiment, the fusion protein is a GST-FCTRX fusion protein in which the FCTRX sequences are fused to the C-terminus of the GST (i.e., glutathione S-transferase) sequences. Such fusion proteins can facilitate the purification of recombinant FCTRX.

In another embodiment, the fusion protein is an FCTRX protein containing a heterologous signal sequence at its N-terminus. For example, the native FCTRX signal sequence can be removed and replaced with a signal sequence from another protein. In certain host cells (e.g., mammalian host cells), expression and/or secretion of FCTRX can be increased through use of a heterologous signal sequence.

In yet another embodiment, the fusion protein is an FCTRX-immunoglobulin fusion protein in which the FCTRX are fused to sequences derived from a member of the immunoglobulin protein family. The FCTRX-immunoglobulin fusion proteins of the invention can be incorporated into pharmaceutical compositions and administered to a subject to inhibit an interaction between an FCTRX ligand and an FCTRX protein on the surface of a cell, to thereby suppress FCTRX-mediated signal transduction in vivo. The FCTRX-immunoglobulin fusion proteins can be used to affect the bioavailability of an FCTRX cognate ligand. Inhibition of the FCTRX ligand/FCTRX interaction are useful therapeutically for both the treatment of proliferative and differentiative disorders, as well as modulating (e.g. promoting or inhibiting) cell survival. Moreover, the FCTRX-immunoglobulin fusion proteins of the invention can be used as immunogens to produce anti-FCTRX antibodies in a subject, to purify FCTRX ligands, and in screening assays to identify molecules that inhibit the interaction of FCTRX with an FCTRX ligand.

An FCTRX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An FCTRX-encoding nucleic acid can be cloned into such an expression vector such that the fusion moiety is linked in-frame to the FCTRX protein.

FCTRX Agonists and Antagonists

The present invention also pertains to variants of the FCTRX proteins that function as either FCTRX agonists (mimetics) or a FCTRX antagonists. Variants of the FCTRX protein can be generated by mutagenesis, e.g., discrete point mutation or truncation of the FCTRX protein. An agonist of the FCTRX protein can retain substantially the same, or a subset of, the biological activities of the naturally occurring form of the FCTRX protein. An antagonist of the FCTRX protein can inhibit one or more of the activities of the naturally occurring form of the FCTRX protein by, for example, competitively binding to a downstream or upstream member of a cellular signaling cascade which includes the FCTRX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the FCTRX proteins.

Variants of the FCTRX protein that function as either FCTRX agonists (mimetics) or as FCTRX antagonists can be identified by screening combinatorial libraries of mutants, e.g., truncation mutants, of the FCTRX protein for FCTRX protein agonist or antagonist activity. In one embodiment, a variegated library of FCTRX variants is generated by combinatorial mutagenesis at the nucleic acid level and is encoded by a variegated gene library. A variegated library of FCTRX variants can be produced by, for example, enzymatically ligating a mixture of synthetic oligonucleotides into gene sequences such that a degenerate set of potential FCTRX sequences is expressible as individual nucleic acids, or alternatively, as a set of larger fusion proteins (e.g., for phage display) containing the set of FCTRX sequences therein. There are a variety of methods which can be used to produce libraries of potential FCTRX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential FCTRX sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the FCTRX protein coding sequence can be used to generate a variegated population of FCTRX fragments for screening and subsequent selection of variants of an FCTRX protein. In one embodiment, a library of coding sequence fragments can be generated by treating a double stranded PCR fragment of an FCTRX coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the FCTRX protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of FCTRX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify FCTRX variants (Arkin and Yourvan (1992) PNAS 89:7811–7815; Delgrave et al. (1993) Protein Engineering 6:327–331).

Anti-FCTRX Antibodies

An isolated FCTRX protein, or a portion of fragment thereof, can be used as an immunogen to generate antibodies that bind FCTRX using standard techniques for polyclonal and monoclonal antibody preparation. The full-length FCTRX protein can be used or, alternatively, the invention provides antigenic peptide fragments of FCTRX for use as immunogens. The antigenic peptide of FCTRX comprises at least 8 amino acid residues of the amino acid sequence shown in SEQ ID NO:3 or 6 and encompasses an epitope of FCTRX such that an antibody raised against the peptide forms a specific immune complex with FCTRX. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of FCTRX that are located on the surface of the protein, e.g., hydrophilic regions.

As disclosed herein, FCTRX protein sequence of SEQ ID NO:3 or 6, or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as FCTRX. Such antibodies include, but are not limited to, polyclonal, monoclonal, chimeric, single chain, $F_{ab}$ and $F_{(ab')2}$ fragments, and an $F_{ab}$ expression library. In a specific embodiment, antibodies to human FCTRX proteins are disclosed. Various procedures known within the art may be used for the production of polyclonal or monoclonal antibodies to an FCTRX protein sequence of SEQ ID NO:3 or 6, or derivative, fragment, analog or homolog thereof.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed FCTRX protein or a chemically synthesized FCTRX polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and Corynebacterium parvum, or similar immunostimulatory agents. If desired, the antibody molecules directed against FCTRX can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of FCTRX. A monoclonal antibody composition thus typically displays a single binding affinity for a particular FCTRX protein with which it immunoreacts. For preparation of monoclonal antibodies directed towards a particular FCTRX protein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 Nature 256: 495–497); the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridoma (see Cote, et al., 1983, Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

According to the invention, techniques can be adapted for the production of single-chain antibodies specific to an FCTRX protein (see e.g., U.S. Pat. No. 4,946,778). In addition, methodologies can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for an FCTRX protein or derivatives, fragments, analogs or homologs thereof. Non-human antibodies can be "humanized" by techniques well known in the art. See e.g., U.S. Pat. No. 5,225,539. Antibody fragments that contain the idiotypes to an FCTRX protein may be produced by techniques known in the art including, but not limited to: (i) an $F_{(ab')2}$ fragment produced by pepsin digestion of an antibody molecule: (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-FCTRX antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240: 1041–1043; Liu et al. (1987) PNAS 84:3439–3443; Liu et al. (1987) J Immunol. 139:3521–3526; Sun et al. (1987) PNAS 84:214–218; Nishimura et al. (1987) Cancer Res 47:999–1005; Wood et al. (1985) Nature 314:446–449; Shaw et al. (1988) J Natl Cancer Inst 80:1553–1559); Morrison (1985) Science 229:1202–1207; Oi et al. (1986) BioTechniques 4:214; U.S. Pat. No. 5,225,539; Jones et al. (1986) Nature 321:552–525; Verhocyan et al. (1988) Science 239:1534; and Beidler et al. (1988) J Immunol 141: 4053–4060.

In one embodiment, methodologies for the screening of antibodies that possess the desired specificity include, but are not limited to, enzyme-linked immunosorbent assay (ELISA) and other immunologically-mediated techniques known within the art.

Anti-FCTRX antibodies may be used in methods known within the art relating to the localization and/or quantitation of an FCTRX protein (e.g., for use in measuring levels of the FCTRX protein within appropriate physiological samples, for use in diagnostic methods, for use in imaging the protein, and the like). In a given embodiment, antibodies for FCTRX proteins, or derivatives, fragments, analogs or homologs thereof, that contain the antibody derived binding domain, are utilized as pharmacologically-active compounds [hereinafter "Therapeutics"].

An anti-FCTRX antibody (e.g., monoclonal antibody) can be used to isolate FCTRX by standard techniques, such as affinity chromatography or immunoprecipitation. An anti-FCTRX antibody can facilitate the purification of natural FCTRX from cells and of recombinantly produced FCTRX expressed in host cells. Moreover, an anti-FCTRX antibody can be used to detect FCTRX protein (e.g., in a cellular lysate or cell supernatant) in order to evaluate the abundance and pattern of expression of the FCTRX protein. Anti-FCTRX antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

FCTRX Recombinant Expression Vectors and Host Cells

Another aspect of the invention pertains to vectors, preferably expression vectors, containing a nucleic acid encoding FCTRX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., FCTRX proteins, mutant forms of FCTRX, fusion proteins, etc.).

The recombinant expression vectors of the invention can be designed for expression of FCTRX in prokaryotic or eukaryotic cells. For example, FCTRX can be expressed in bacterial cells such as *E. coli,* insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inductible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc: Smith and Johnson (1988) *Gene* 67:31–40), pMAI, (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, GENE EXPRESSION TECHNOLOGY: METHODS IN EENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the FCTRX expression vector is a yeast expression vector Examples of vectors for expression in yeast *S. cerivisae* include pYepSec1 (Baldari et al., (1987) *EMBO J* 6:229–234), pMFa (Kurjan and Kerskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, FCTRX can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156–2165) and the pVL series (Lucklow and Summers (1980) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187–195). When used in mammalian cells, the expression vector's control functions are often provided by viral regulatory elements. For example, commonly used promoters are derived from polyoma. Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL, 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to FCTRX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, FCTRX protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL, 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding FCTRX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) FCTRX protein. Accordingly, the invention further provides methods for producing FCTRX protein using the host cells of the invention. In one embodiment, the method comprises culturing the host cell of invention (into which a recombinant expression vector encoding FCTRX has been introduced) in a suitable medium such that FCTRX protein is produced. In another embodiment, the method further comprises isolating FCTRX from the medium or the host cell.

Transgenic Animals

The host cells of the invention can also be used to produce nonhuman transgenic animals. For example, in one embodiment, a host cell of the invention is a fertilized oocyte or an embryonic stem cell into which FCTRX-coding sequences have been introduced. Such host cells can then be used to create non-human transgenic animals in which exogenous FCTRX sequences have been introduced into their genome or homologous recombinant animals in which endogenous FCTRX sequences have been altered. Such animals are useful for studying the function and/or activity of FCTRX and for identifying and/or evaluating modulators of FCTRX activity. As used herein, a "transgenic animal" is a non-human animal, preferably a mammal, more preferably a rodent such as a rat or mouse, in which one or more of the cells of the animal includes a transgenic. Other examples of transgenic animals include non-human primates, sheep, dogs, cows, goats, chickens, amphibans, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous FCTRX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing FCTRX-encoding nucleic acid into the male pronuclei of a fertilized oocyte, e.g., by microinjection, retroviral infection, and allowing the oocyte to develop in a pseudopregnant female foster animal. The human FCTRX cDNA sequence of SEQ ID NO:1, 2, 4, or 5 can be introduced as a transgene into the genome of a non-human animal. Alternatively, a nonhuman homologue of the human FCTRX gene, such as a mouse FCTRX gene, can be isolated based on hybridization to the human FCTRX cDNA (described further above) and used as a transgene. Intronic sequences and polyadenylation signals can also be included in the transgene to increase the efficiency of expression of the transgene. A tissue-specific regulatory sequence(s) can be operably linked to the FCTRX transgene to direct expression of FCTRX protein to particular cells. Methods for generating transgenic animals via embryo manipulation and microinjection, particularly animals such as mice, have become conventional in the art and are described, for example, in U.S. Pat. No. 4,736,866; 4,870,009; and 4,873, 191; and Hogan 1986, In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the FCTRX transgene in its genome and/or expression of FCTRX mRNA in tissues or cells of the animals. A transgenic founder animal can then be used to breed additional animals carrying the transgene. Moreover, transgenic animals carrying a transgene encoding FCTRX can further be bred to other transgenic animals carrying other transgenes.

To create a homologous recombinant animal, a vector is prepared which contains at least a portion of a FCTRX gene into which a deletion, addition or substitution has been introduced to thereby alter, e.g., functionally disrupt, the FCTRX gene. The FCTRX gene can be a human gene (e.g., the cDNA of SEQ ID NO:1, 2, 4, or 5) but more preferably, is a non-human homologue of a human FCTRX gene. For example, a mouse homologue of human FCTRX gene of SEQ ID NO:1, 2, 4, or 5 can be used to construct a homologous recombination vector suitable for altering an endogenous FCTRX gene in the mouse genome. In one embodiment, the vector is designed such that, upon homologous recombination, the endogenous FCTRX gene is functionally disrupted (i.e., no longer encodes a functional protein; also referred to as a "knock out" vector).

Alternatively, the vector can be designed such that, upon homologous recombination, the endogenous FCTRX gene is mutated or otherwise altered but still encodes functional protein (e.g., the upstream regulatory region can be altered to thereby alter the expression of the endogenous FCTRX protein). In the homologous recombination vector, the altered portion of the FCTRX gene is flanked at its 5' and 3' ends by additional nucleic acid of the FCTRX gene to allow for homologous recombination to occur between the exogenous FCTRX gene carried by the vector and an endogenous FCTRX gene in an embryonic stem cell. The additional flanking FCTRX nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced FCTRX gene has homologously recombined with the endogenous FCTRX gene are selected (see e.g., Li et al. (1992) *Cell* 69:915).

The selected cells are then injected into a blastocyst of an animal (e.g., a mouse) to form aggregation chimeras. See e.g., Bradley 1987, In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr Opin Biotechnol* 2:283–829; PCT International Publication Nos.: WO 90/11354; WO 91/01140; WO 92/0968; and WO 93/04169.

In another embodiment, transgenic non-human animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The FCTRX nucleic acid molecules, FCTRX proteins, and anti-FCTRX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an FCTRX protein or anti-FCTRX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

USES AND METHODS OF THE INVENTION

The isolated nucleic acid molecules of the invention can be used to express FCTRX protein (e.g., via a recombinant expression vector in a host cell in gene therapy applications), to detect FCTRX mRNA (e.g., in a biological sample) or a genetic lesion in an FCTRX gene, and to modulate FCTRX activity, as described further below. In addition, the FCTRX proteins can be used to screen drugs or compounds that modulate the FCTRX activity or expression as well as to treat disorders characterized by insufficient or excessive production of FCTRX protein or production of FCTRX protein forms that have decreased or aberrant activity compared to FCTRX wild type protein (e.g. proliferative disorders such as cancer or preclampsia, immune system disorders and inflammation, neurological disorders, and skin and muscle abnormalities). In addition, the anti-FCTRX antibodies of the invention can be used to detect and isolate FCTRX proteins and modulate FCTRX activity.

This invention further pertains to novel agents identified by the above described screening assays and uses thereof for treatments as described herein.

Screening Assays

The invention provides a method (also referred to herein as a "screening assay" for identifying modulators, i.e., candidate or test compounds or agents (e.g., peptides, peptidomimetics, small molecules or other drugs) that bind to FCTRX proteins or have a stimulatory or inhibitory effect on, for example, FCTRX expression or FCTRX activity.

In one embodiment, the invention provides assays for screening candidate or test compounds which bind to or modulate the activity of a membrane-bound form of an FCTRX protein or polypeptide or biologically active portion thereof. The test compounds of the present invention can be obta4ined using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *Biotechniques* 13:412–421), or on beads (Lam (1991) *Nature* 354:82–84), on chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991) *J Mol Biol* 222:301–310; Ladner above.).

In one embodiment, an assay is a cell-based assay in which a cell which expresses a membrane-bound form of FCTRX protein, or a biologically active portion thereof, on the cell surface is contacted with a test compound and the ability of the test compound to bind to an FCTRX protein is determined. The cell, for example, can be of mammalian origin or a yeast cell. Determining the ability of the test compound to bind to the FCTRX protein can be accomplished, for example, by coupling the test compound with a radioisotope or enzymatic label such that binding of the test compound to the FCTRX protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of FCTRX protein, or a biologically active portion thereof, on the cell surface with a known compound which binds FCTRX to form an assay mixture, contacting the assay mixture with a test compound, and determining the ability of the test compound to interact with FCTRX protein, wherein determining the ability of the test compound to interact with an FCTRX protein comprises determining the ability of the test compound to preferentially bind to FCTRX or a biologically active portion thereof as compared to the known compound.

In another embodiment, an assay is cell-based assay comprising contacting a cell expressing a membrane-bound form of FCTRX protein, or a biologically active portion thereof, on the cell surface with a test compound and determining the ability of the test compound to modulate (e.g., stimulate or inhibit) the activity of the FCTRX protein or biologically active portion thereof. Determining the ability of the test compound to modulate the activity of FCTRX or a biologically active portion thereof can be accomplished, for example, by determining the ability of the FCTRX protein to bind to or interact with an FCTRX target molecule. As used herein, a "target molecule" is a molecule with which an FCTRX protein binds or interacts in nature, for example, a molecule on the surface of a cell which expresses an FCTRX protein, a molecule on the surface of a second cell, a molecule in the extracellular milieu, a molecule associated with the internal surface of a cell membrane or a cytoplasmic molecule. An FCTRX target molecule can be a non-FCTRX molecule or an FCTRX protein or polypeptide of the present invention. In one embodiment, an FCTRX target molecule is a component of a signal transduction pathway that facilitates transduction of an extracellular signal (e.g. a signal generated by binding of a compound to a membrane-bound FCTRX molecule) through the cell membrane and into the cell. The target, for example, can be a second intracellular protein that has catalytic activity or a protein that facilitates the association of downstream signaling molecules with FCTRX.

Determining the ability of the FCTRX protein to bind to or interact with an FCTRX target molecule can be accomplished by one of the methods described above for determining direct binding. In one embodiment, determining the ability of the FCTRX protein to bind to or interact with an FCTRX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an FCTRX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting an / protein or biologically active portion thereof with a test compound and determining the ability of the test compound to bind to the FCTRX protein or biologically active portion thereof. Binding of the test compound to the FCTRX protein can be determined either directly or indirectly as described above. In one embodiment, the assay comprises contacting the FCTRX protein or biologically active portion thereof with a known compound which binds FCTRX to form an assay mixture, contacting the assay mixture with a test compound, and determining the ability of the test compound to interact with an FCTRX protein, where determining the ability of the test compound to interact with an / protein comprises determining the ability of the test compound to preferentially bind to FCTRX or biologically active portion thereof as compared to the known compound.

In another embodiment, an assay is a cell-free assay comprising contacting FCTRX protein or biologically active portion thereof with a test compound and determining the ability of the test compound to modulate (e.g. stimulate or inhibit) the activity of the FCTRX protein or biologically active portion thereof. Determining the ability of the test compound to modulate the activity of FCTRX can be accomplished, for example, by determining the ability of the FCTRX protein to bind to an FCTRX target molecule by one of the methods described above for determining direct binding. In an alternative embodiment, determining the ability of the test compound to modulate the activity of FCTRX can be accomplished by determining the ability of the FCTRX protein further modulate an FCTRX target molecule. For example, the catalytic/enzymatic activity of the target molecule on an appropriate substrate can be determined as previously described.

In yet another embodiment, the cell-free assay comprises contacting the FCTRX protein or biologically active portion thereof with a known compound which binds FCTRX to form an assay mixture, contacting the assay mixture with a test compound, and determining the ability of the test compound to interact with an FCTRX protein, wherein determining the ability of the test compound to interact with an FCTRX protein comprises determining the ability of the FCTRX protein to preferentially bind to or modulate the activity of an FCTRX target molecule.

The cell-free assays of the present invention are amenable to use of both the soluble form or the membrane-bound form of FCTRX. In the case of cell-free assays comprising the membrane-bound form of FCTRX, it may be desirable to utilize a solubilizing agent such that the membrane-bound form of FCTRX is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-(3-cholamidopropyl)dimethylamminiol-1-propane sulfonate (CHAPS), 3-(3-cholamidopropyl)dimethylamminiol-2-hydroxy-1-propane sulfonate (CHAPSO), or N-dodecyl--N,N-dimethyl-3-ammonio-1-propane sulfonate.

In more than one embodiment of the above assay methods of the present invention, it may be desirable to immobilize either FCTRX or its target molecule to facilitate separation of complexed from uncomplexed forms of one or both of the proteins, as well as to accommodate automation of the assay.

Binding of a test compound to FCTRX, or interaction of FCTRX with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-FCTRX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or FCTRX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of FCTRX binding or activity determined using standard techniques.

Other techniques for immobilizing proteins on matrices can also be used in the screening assays of the invention. For example, either FCTRX or its target molecule can be immobilized utilizing conjugation of biotin and streptavidin. Biotinylated FCTRX or target molecules can be prepared from biotin-NIIS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with FCTRX or target molecules, but which do not interfere with binding of the FCTRX protein to its target molecule, can be derivatized to the wells of the plate, and unbound target or FCTRX trapped in the wells by antibody conjugation. Methods for detecting such complexes, in addition to those described above for the GST-immobilized complexes, include immunodetection of complexes using antibodies reactive with the FCTRX or target molecule, as well as enzyme-linked assays that rely on detecting an enzymatic activity associated with the FCTRX or target molecule.

In another embodiment, modulators of FCTRX expression are identified in a method wherein a cell is contacted with a candidate compound and the expression of FCTRX mRNA or protein in the cell is determined. The level of expression of FCTRX mRNA or protein in the presence of the candidate compound is compared to the level of expression of FCTRX mRNA or protein in the absence of the candidate compound. The candidate compound can then be identified as a modulator of FCTRX expression based on this comparison. For example, when expression of FCTRX mRNA or protein is greater (statistically significantly greater) in the presence of the candidate compound than in its absence, the candidate compound is identified as a stimulator of FCTRX mRNA or protein expression. Alternatively, when expression of FCTRX mRNA or protein is less (statistically significantly less) in the presence of the candidate compound than in its absence, the candidate compound is identified as an inhibitor of FCTRX mRNA or protein expression. The level of FCTRX mRNA or protein expression in the cells can be determined by methods described herein for detecting FCTRX mRNA or protein.

In yet another aspect of the invention, the FCTRX proteins can be used as "bait proteins" in a two-hybrid assay or three hybrid assay (see, e.g., U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), to identify other proteins that bind to or interact with FCTRX ("FCTRX-binding proteins" or "FCTRX-bps") and modulate FCTRX activity. Such FCTRX-binding proteins are also likely to be involved in the propagation of signals by the FCTRX proteins as, for example, upstream or downstream elements of the FCTRX pathway.

The two-hybrid system is based on the modular nature of most transcription factors, which consist of separable DNA-binding and activation domains. Briefly, the assay utilizes two different DNA constructs. In one construct, the gene that codes for FCTRX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a FCTRX-dependent complex, the DNA-binding and activation domains of the transcription factor are brought into close FCTRXimity. This FCTRXimity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with FCTRX.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the FCTRX, sequences, described herein, can be used to map the location of the FCTRX genes, respectively, on a chromosome. The mapping of the FCTRX sequences to chromosomes is an important first step in correlating these sequences with genes associated with disease.

Briefly, FCTRX genes can be mapped to chromosomes by preparing PCR primers (preferably 15–25 bp in length) from the FCTRX sequences. Computer analysis of the FCTRX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the FCTRX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the FCTRX sequences to design oligonucleotide primers, sublocalization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see Verma et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, for example, in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, for example, Egeland et al. (1987) *Nature,* 325:783–787.

Moreover, differences in the DNA sequences between individuals affected and unaffected with a disease associated with the FCTRX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The FCTRX sequences of the present invention can also be used to identify individuals from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the FCTRX sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The FCTRX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. For example, the noncoding sequences of SEQ ID NO:1, 2, 4, or 5 can comfortably provide positive individual identification with a panel of perhaps 10 to 1,000 primers that each yield a noncoding amplified sequence of 100 bases. If predicted coding sequences, such as the nucleic acid sequences that code for the amino acid sequences of SEQ ID NO:3 or 6 are used, a more appropriate number of primers for positive individual identification would be 500–2,000.

Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining FCTRX protein and/or nucleic acid expression as well as FCTRX activity, in the context of a biological sample (e.g., blood, serum, cells, tissue) to thereby determine whether an individual is afflicted with a disease or disorder, or is at risk of developing a disorder, associated with aberrant FCTRX expression or activity. The invention also provides for prognostic (or predictive) assays for determining whether an individual is at risk of developing a disorder associated with FCTRX protein, nucleic acid expression or activity. For example, mutations in an FCTRX gene can be assayed in a biological sample. Such assays can be used for prognostic or predictive purpose to thereby prophylactically treat an individual prior to the onset of a disorder characterized by or associated with FCTRX protein, nucleic acid expression or activity.

Another aspect of the invention provides methods for determining FCTRX protein, nucleic acid expression or FCTRX activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs, compounds) on the expression or activity of FCTRX in clinical trials.

These and other agents are described in further detail in the following sections.

Diagnostic Assays

An exemplary method for detecting the presence or absence of FCTRX in a biological sample involves obtaining a biological sample from a test subject and contacting the biological sample with a compound or an agent capable of detecting FCTRX protein or nucleic acid (e.g., mRNA, genomic DNA) that encodes FCTRX protein such that the presence of FCTRX is detected in the biological sample. An agent for detecting FCTRX mRNA or genomic DNA is a labeled nucleic acid probe capable of hybridizing to FCTRX mRNA or genomic DNA. The nucleic acid probe can be, for example, a full-length FCTRX nucleic acid, such as the nucleic acid of SEQ ID NO:1, 2, 4, or 5, or a portion thereof, such as an oligonucleotide of at least 15, 30, 50, 100, 250 or 500 nucleotides in length and sufficient to specifically hybridize under stringent conditions to FCTRX mRNA or genomic DNA. Other suitable probes for use in the diagnostic assays of the invention are described herein.

An agent for detecting FCTRX protein is an antibody capable of binding to FCTRX protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect FCTRX mRNA, protein, or genomic DNA in a biological sample in vitro as well as in vivo. For example, in vitro techniques for detection of FCTRX mRNA include Northern hybridizations and in situ hybridizations. In vitro techniques for detection of FCTRX protein include enzyme linked immunosorbent assays (ELISAs), Western blots, immunoprecipitations and immunofluorescence, in vitro techniques for detection of FCTRX genomic DNA include Southern hybridizations. Furthermore, in vivo techniques for detection of FCTRX protein include introducing into a subject a labeled anti-FCTRX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting FCTRX protein, mRNA, or genomic DNA, such that the presence of FCTRX protein, mRNA or genomic DNA is detected in the biological sample, and comparing the presence of FCTRX protein, mRNA or genomic DNA in the control sample with the presence of FCTRX protein, mRNA or genomic DNA in the test sample.

The invention also encompasses kits for detecting the presence of FCTRX in a biological sample. For example, the kit can comprise: a labeled compound or agent capable of detecting FCTRX protein or mRNA in a biological sample; means for determining the amount of FCTRX in the sample; and means for comparing the amount of FCTRX in the sample with a standard. The compound or agent can be packaged in a suitable container. The kit can further comprise instructions for using the kit to detect FCTRX protein or nucleic acid.

Prognostic Assays

The diagnostic methods described herein can furthermore be utilized to identify subjects having or at risk of developing a disease or disorder associated with aberrant FCTRX expression or activity. For example, the assays described herein, such as the preceding diagnostic assays or the following assays, can be utilized to identify a subject having or at risk of developing a disorder associated with FCTRX protein, nucleic acid expression or activity such as cancer or fibrotic disorders. Alternatively, the prognostic assays can be utilized to identify a subject having or at risk for developing a disease or disorder. Thus, the present invention provides a method for identifying a disease or disorder associated with aberrant FCTRX expression or activity in which a test sample is obtained from a subject and FCTRX protein or nucleic acid (e.g., mRNA, genomic DNA) is detected, wherein the presence of FCTRX protein or nucleic acid is diagnostic for a subject having or at risk of developing a disease or disorder associated with aberrant FCTRX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant FCTRX expression or activity. For example, such methods can be used to determine whether a subject can be effectively treated with an agent for a disorder, such as cancer or preeclampsia. Thus, the present invention provides methods for determining whether a subject can be effectively treated with an agent for a disorder associated with aberrant FCTRX expression or activity in which a test sample is obtained and FCTRX protein or nucleic acid is detected (e.g., wherein the presence of FCTRX protein or nucleic acid is diagnostic for a subject that can be administered the agent to treat a disorder associated with aberrant FCTRX expression or activity.)

The methods of the invention can also be used to detect genetic lesions in an FCTRX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an FCTRX-protein, or the mis-expression of the FCTRX gene. For example, such genetic lesions can be detected by ascertaining the existence of at least one of (1) a deletion of one or more nucleotides from an FCTRX gene; (2) an addition of one or more nucleotides to an FCTRX gene; (3) a substitution of one or more nucleotides of an FCTRX gene, (4) a chromosomal rearrangement of an FCTRX gene; (5) an alteration in the level of a messenger RNA transcript of an FCTRX gene, (6) aberrant modification of an FCTRX gene, such as of the methylation pattern of the genomic DNA, (7) the presence of a non-wild type splicing pattern of a messenger RNA transcript of an FCTRX gene, (8) a non-wild type level of an FCTRX-protein, (9) allelic loss of an FCTRX gene, and (10) inappropriate post-translational modification of an FCTRX-protein. As described herein, there are a large number of assay techniques known in the art which can be used for detecting lesions in an FCTRX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in an FCTRX-gene (see Abravaya et al. (1995) *Nucl Acids Res* 23:675–682). This method can include the steps of collecting a sample of cells from a patient, isolating nucleic acid (e.g., genomic, mRNA or both) from the cells of the sample, contacting the nucleic acid sample with one or more primers that specifically hybridize to an FCTRX gene under conditions such that hybridization and amplification of the FCTRX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, *Proc Natl Acad Sci USA* 87:1874–1878), transcriptional amplification system (Kwoh, et al., 1989, *Proc Natl Acad Sic USA* 86:1173–1177), Q-Beta Replicase (Lizardi et al. 1988, *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an FCTRX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicate mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in FCTRX can be identified by hybridizing a sample and control nucleic acids, e.g., DNA or RNA, to high density arrays containing hundreds or thousands of oligonucleotides probes (Cronin et al. (1996) *Human Mutation* 7: 244–255; Kozal et al. (1996) *Nature Medicine* 2: 753–759). For example, genetic mutations in FCTRX can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the FCTRX gene and detect mutations by comparing the sequence of the sample FCTRX with the corresponding wild-type (control) sequence. Examples of sequencing reactions include those based on techniques developed by Maxim and Gilbert (1977) *PNAS* 74:560 or Sanger (1977) *PNAS* 74:5463. It is also contemplated that any of a variety of automated sequencing procedures can be utilized when performing the diagnostic assays (Naeve et al., (1995) *Biotechniques* 19:448), including sequencing by mass spectrometry (see, e.g., PCT International Publ. No. WO 94/16101; Cohen et al. (1996) *Adv Chromatogr* 36:127–162; and Griffin et al. (1993) *Appl Biochem Biotechnol* 38:147–159).

Other methods for detecting mutations in the FCTRX gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type FCTRX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397; Saleeba et al (1992) *Methods Enzymol* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in FCTRX cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an FCTRX sequence, e.g., a wild-type FCTRX sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in FCTRX genes. For example, single strand conformation polymorphism (SSCP) may be used to detect differences in electrophoretic mobility between mutant and wild type nucleic acids (Orita et al. (1989) *Proc Natl Acad Sci USA:* 86:2766, see also Cotton (1993) *Mutat Res* 285:125–144; Hayashi (1992) *Genet Anal Tech Appl* 9:73–79). Single-stranded DNA fragments of sample and control FCTRX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of apFCTRXimately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al (1992) *Mol Cell Probes* 6:1). It is anticipated that in certain embodiments amplification may also be performed using Taq ligase for amplification (Barany (1991) *Proc Natl Acad Sci USA* 88:189). In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an FCTRX gene.

Furthermore, any cell type or tissue, preferably peripheral blood leukocytes, in which FCTRX is expressed may be utilized in the prognostic assays described herein. However, any biological sample containing nucleated cells may be used, including, for example, buccal mucosal cells.

Pharmacogenomics

Agents, or modulators that have a stimulatory or inhibiting effect on FCTRX activity (e.g., FCTRX gene expression), as identified by a screening assay described herein can be administered to individuals to treat (prophylactically or therapeutically) disorders (e.g., cancer or immune disorders, neurological disorders, muscular dystrophy, or epidermolysis bullosa simplex) associated with aberrant FCTRX activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimes. Accordingly, the activity of FCTRX protein, expression of FCTRX nucleic acid, or mutation content of FCTRX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons.

See e.g., Eichelbaum, *Clin Exp Pharmacol Physiol,* 1996, 23:983–985 and Linder, *Clin Chem,* 1997, 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme is the so called ultra-rapid metabolizers who do not respond to standard doses. Recently, the molecular basis of ultra-rapid metabolism has been identified to be due to CYP2D6 gene amplification.

Thus, the activity of FCTRX protein, expression of FCTRX nucleic acid, or mutation content of FCTRX genes in an individual can be determined to thereby select appropriate agent(s) for therapeutic or prophylactic treatment of the indivdual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an FCTRX modulator, such as a modulator identified by one of the exemplary screening assays described herein.

Monitoring of Effects During Clinical Trials

Monitoring the influence of agents (e.g., drugs, compounds) on the expression or activity of FCTRX (e.g., the ability to modulate aberrant cell proliferation and/or differentiation) can be applied not only in basic drug screening, but also in clinical trials. For example, the effectiveness of an agent determined by a screening assay as described herein to increase FCTRX gene expression, protein levels, or upregulate FCTRX activity, can be monitored in clinical trails of subjects exhibiting decreased FCTRX gene expression, protein levels, or downregulated FCTRX activity. Alternatively, the effectiveness of an agent determined by a screening assay to decrease FCTRX gene expression, protein levels, or downregulate FCTRX activity, can be monitored in clinical trails of subjects exhibiting increased FCTRX gene expression, protein levels, or upregulated FCTRX activity. In such clinical trials, the expression or activity of FCTRX and, preferably, other genes that have been implicated in, for example, a cellular proliferation disorder can be used as a "read out" or markers of the immune responsiveness of a particular cell.

For example, and not by way of limitation, genes, including FCTRX, that are modulated in cells by treatment with an agent (e.g., compound, drug or small molecule) that modulates FCTRX activity (e.g., identified in a screening assay as described herein) can be identified. Thus, to study the effect of agents on cellular proliferation disorders, for example, in a clinical trial, cells can be isolated and RNA prepared and analyzed for the levels of expression of FCTRX and other genes implicated in the disorder. The levels of gene expression (i.e., a gene expression pattern) can be quantified by Northern blot analysis of RT-PCR, as described herein, or alternatively by measuring the amount of protein produced, by one of the methods as described herein, or by measuring the levels of activity of FCTRX or other genes. In this way, the gene expression pattern can serve as a marker,indicative of the physiological response of the cells to the agent. Accordingly, this response state may be determined before, and at various points during, treatment of the individual with the agent.

In one embodiment, the present invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an FCTRX protein, mRNA, or genomic DNA in the preadministration sample; (iii) obtaining one or more post-administration samples from the subject; (iv) detecting the level of expression or activity of the FCTRX protein, mRNA, or genomic DNA in the post-administration samples; (v) comparing the level of expression or activity of the FCTRX protein, mRNA, or genomic DNA in the pre-administration sample with the FCTRX protein, mRNA, or genomic DNA in the post administration sample or samples; and (vi) altering the administration of the agent to the subject accordingly. For example, increased administration of the agent may be desirable to increase the expression or activity of FCTRX to higher levels than detected, i.e., to increase the effectiveness of the agent. Alternatively, decreased administration of the agent may be desirable to decrease expression or activity of FCTRX to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant FCTRX expression or activity.

Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989, Science 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic Methods

In one aspect, the invention provides a method for preventing, in a subject, a disease or condition associated with an aberrant FCTRX expression or activity, by administering to the subject an agent that modulates FCTRX expression or at least one FCTRX activity. Subjects at risk for a disease that is caused or contributed to by aberrant FCTRX expression or activity can be identified by, for example, any or a combination of diagnostic or prognostic assays as described herein. Administration of a prophylactic agent can occur prior to the manifestation of symptoms characteristic of the FCTRX aberrancy, such that a disease or disorder is prevented or, alternatively, delayed in its progression. Depending on the type of FCTRX aberrancy, for example, an FCTRX agonist or FCTRX antagonist agent can be used for treating the subject. The appropriate agent can be determined based on screening assays described herein. The prophylactic methods of the present invention are further discussed in the following subsections.

Therapeutic Methods

Another aspect of the invention pertains to methods of modulating FCTRX expression or activity for therapeutic purposes. The modulatory method of the invention involves contacting a cell with an agent that modulates one or more of the activities of FCTRX protein activity associated with the cell. An agent that modulates FCTRX protein activity can be an agent as described herein, such as a nucleic acid or a protein, a naturally-occurring cognate ligand of an FCTRX protein, a peptide, an FCTRX peptidomimetic, or other small molecule. In one embodiment, the agent stimulates one or more FCTRX protein activity. Examples of such stimulatory agents include active FCTRX protein and a nucleic acid molecule encoding FCTRX that has been introduced into the cell. In another embodiment, the agent inhibits one or more FCTRX protein activity. Examples of such inhibitory agents include antisense FCTRX nucleic acid molecules and anti-FCTRX antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an FCTRX protein or nucleic acid molecule. In one embodiment, the method involves administering an agent (e.g., an agent identified by a screening assay described herein), or combination of agents that modulates (e.g., upregulates or downregulates) FCTRX expression or activity. In another embodiment, the method involves administering an FCTRX protein or nucleic acid molecule as therapy to compensate for reduced or aberrant FCTRX expression or activity.

Stimulation of FCTRX activity is desirable in situations in which FCTRX is abnormally downregulated and/or in which increased FCTRX activity is likely to have a beneficial effect. One example of such a situation is where a subject has a disorder characterized by aberrant cell proliferation and/or differentiation (e.g., cancer). Another example of such a situation is where the subject has a gestational disease (e.g., preclampsia).

DISEASE PATHWAYS

Determination of the Biological Effect of the Therapeutic

In various embodiments of the present invention, suitable in vitro and in vivo assays are utilized to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model systems known in the art may be used prior to administration to human subjects.

Malignancies

An aforementioned protein is involved in the regulation of cell proliferation. Accordingly, Therapeutics of the present invention are useful in the therapeutic or prophylactic treatment of diseases or disorders that are associated with cell hyperproliferation and/or loss of control of cell proliferation (e.g., cancers, malignancies and tumors). For a review of such hyperproliferation disorders, see e.g., Fishman, et al., 1985, MEDICINE, 2nd ed., J. B. Lippincott Co., Philadelphia, Pa.

Therapeutics of the present invention may be assayed by any method known within the art for efficacy in treating or preventing malignancies and related disorders. Such assays include, but are not limited to, in vitro assays utilizing transformed cells or cells derived from the patient's tumor, as well as in vivo assays using animal models of cancer or malignancies. Potentially effective Therapeutics are those that, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing or agonizing) activity, that cancer or malignancy may subsequently be treated or prevented by the administration of a Therapeutic that serves to modulate protein function.

Premalignant Conditions

The Therapeutics of the present invention that are effective in the therapeutic or prophylactic treatment of cancer or maliganancies may also be administered for the treatment of pre-malignant conditions and/or to prevent the progression of a pre-malignancy to a neoplastic or malignant state. Such prophylactic or therapeutic use is indicated in conditions known or suspected of preceding progression to neoplasia or cancer, in particular, where non-neoplastic cell growth consisting of hyperplasia, metaplasia or, most particularly, dysplasia has occurred. For a review of such abnormal cell growth see e.g., Robbins & Angell, 1976, BASIC PATHOLOGY, 2nd ed., W.B. Saunders Co., Philadelphia, Pa.

Hyperplasia is a form of controlled cell proliferation involving an increase in cell number in a tissue or organ, without significant alteration in its structure or function. For example, it has been demonstrated that endometrial hyperplasia often precedes endometrial cancer. Metaplasia is a form of controlled cell growth in which one type of mature or fully differentiated cell substitutes for another type of mature cell. Metaplasia may occur in epithelial or connective tissue cells. Dysplasia is generally considered a precursor of cancer, and is found mainly in the epithelia. Dysplasia is the most disorderly form of non-neoplastic cell growth, and involves a loss in individual cell uniformity and in the architectural orientation of cells. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed or malignant phenotype displayed either in vivo or in vitro within a cell sample derived from a patient, is indicative of the desirability of prophylactic/therapeutic administration of a Therapeutic that possesses the ability to modulate activity of An aforementioned protein. Characteristics of a transformed phenotype include, but are not limited to: (i) morphological changes; (ii) looser substratum attachment; (iii) loss of cell-to-cell contact inhibition; (iv) loss of anchorage dependence; (v) protease release; (vi) increased sugar transport; (vii) decreased serum requirement; (viii) expression of fetal antigens, (ix) disappearance of the 250 kDal cell-surface protein, and the like. See e.g., Richards, et al., 1986, MOLECULAR PATHOLOGY, W.B. Sauders Co., Philadelphia, Pa.

In a specific embodiment of the present invention, a patient that exhibits one or more of the following predisposing factors for malignancy is treated by administration of an effective amount of a Therapeutic: (i) a chromosomal translocation associated with a malignancy (e.g., the Philadelphia chromosome (ber/abl) for chronic myelogenous leukemia and t(14;18) for follicular lymphoma, etc.); (ii) familial polyposis or Gardner's syndrome (possible forerunners of colon cancer); (iii) monoclonal gammopathy of undetermined significance (a possible precursor of multiple myeloma) and (iv) a first degree kinship with persons having a cancer or pre-cancerous disease showing a Mendelian (genetic) inheritance pattern (e.g., familial polyposis of the colon, Gardner's syndrome, hereditary exostosis, polyendocrine adenomatosis, Peutz-Jeghers syndrome, neurofibromatosis of Von Recklinghausen, medullary thyroid carcinoma with amyloid production and pheochromocytoma, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia and Bloom's syndrome).

In another embodiment, a Therapeutic of the present invention is administered to a human patient to prevent the progression to breast, colon, lung, pancreatic, or uterine cancer, or melanoma or sarcoma.

Hyperproliferative and Dysproliferative Disorders

In one embodiment of the present invention, a Therapeutic is administered in the therapeutic or prophylactic treatment of hyperproliferative or benign dysproliferative disorders. The efficacy in treating or preventing hyperproliferative diseases or disorders of a Therapeutic of the present invention may be assayed by any method known within the art. Such assays include in vitro cell proliferation assays, in vitro or in vivo assays using animal models of hyperproliferative diseases or disorders, or the like. Potentially effective Therapeutics may, for example, promote cell proliferation in culture or cause growth or cell proliferation in animal models in comparison to controls.

Specific embodiments of the present invention are directed to the treatment or prevention of cirrhosis of the liver (a condition in which scarring has overtaken normal liver regeneration processes); treatment of keloid (hypertrophic scar) formation causing disfiguring of the skin in which the scarring process interferes with normal renewal; psoriasis (a common skin condition characterized by excessive proliferation of the skin and delay in proper cell fate determination); benign tumors; fibrocystic conditions and tissue hypertrophy (e.g., benign prostatic hypertrophy).

Neurodegenerative Disorders

FCTRX has been implicated in the deregulation of cellular maturation and apoptosis, which are both characteristic of neurodegenerative disease. Accordingly, Therapeutics of the invention, particularly but not limited to those that modulate (or supply) activity of an aforementioned protein, may be effective in treating or preventing neurodegenerative disease. Therapeutics of the present invention that modulate the activity of an aforementioned protein involved in neurodegenerative disorders can be assayed by any method known in the art for efficacy in treating or preventing such neurodegenerative diseases and disorders. Such assays include in vitro assays for regulated cell maturation or inhibition of apoptosis or in vivo assays using animal models of neurodegenerative diseases or disorders, or any of the assays described below. Potentially effective Therapeutics, for example but not by way of limitation, promote regulated cell maturation and prevent cell apoptosis in culture, or reduce neurodegeneration in animal models in comparison to controls.

Once a neurodegenerative disease or disorder has been shown to be amenable to treatment by modulation activity, that neurodegenerative disease or disorder can be treated or prevented by administration of a Therapeutic that modulates activity. Such diseases include all degenerative disorders involved with aging, especially osteoarthritis and neurodegenerative disorders.

Disorders Related to Organ Transplantation

FCTRX has been implicated in disorders related to organ transplantation, in particular but not limited to organ rejection. Therapeutics of the invention, particularly those that modulate (or supply) activity, may be effective in treating or preventing diseases or disorders related to organ transplantation. Therapeutics of the invention (particularly Therapeutics that modulate the levels or activity of an aforementioned protein) can be assayed by any method known in the art for efficacy in treating or preventing such diseases and disorders related to organ transplantation. Such assays include in vitro assays for using cell culture models as described below, or in vivo assays using animal models of diseases and disorders related to organ transplantation, see, e.g., below. Potentially effective Therapeutics, for example but not by way of limitation, reduce immune rejection responses in animal models in comparison to controls.

Accordingly, once diseases and disorders related to organ transplantation are shown to be amenable to treatment by modulation of activity, such diseases or disorders can be treated or prevented by administration of a Therapeutic that modulates activity.

Cardiovascular Disease

FCTRX has been implicated in cardiovascular disorders, including in atherosclerotic plaque formation. Diseases such as cardiovascular disease, including cerebral thrombosis or hemorrhage, ischemic heart or renal disease, peripheral vascular disease, or thrombosis of other major vessel, and other diseases, including diabetes mellitus, hypertension, hypothyroidism, cholesterol ester storage disease, systemic lupus erythematosus, homocysteinemia, and familial protein or lipid processing diseases, and the like, are either directly or indirectly associated with atherosclerosis. Accordingly, Therapeutics of the invention, particularly those that modulate (or supply) activity or formation may be effective in treating or preventing atherosclerosis-associated diseases or disorders. Therapeutics of the invention (particularly Therapeutics that modulate the levels or activity) can be assayed by any method known in the art, including those described below, for efficacy in treating or preventing such diseases and disorders.

A vast array of animal and cell culture models exist for processes involved in atherosclerosis. A limited and non-exclusive list of animal models includes knockout mice for premature atherosclerosis (Kurabayashi and Yazaki, 1996, Int. Angiol. 15: 187–194), transgenic mouse models of atherosclerosis (Kappel et al., 1994, FASEB J, 8: 583–592), antisense oligonucleotide treatment of animal models (Callow, 1995, Curr. Opin. Cardiol. 10: 569–576), transgenic rabbit models for atherosclerosis (Taylor, 1997, Ann. N.Y. Acad. Sci 811: 146–152), hypercholesterolemic animal models (Rosenfeld, 1996, Diabetes Res. Clin. Pract. 30 Suppl.: 1–11), hyperlipidemic mice (Paigen et al., 1994, Curr. Opin. Lipidol. 5: 258–264), and inhibition of lipoxygenase in animals (Sigal et al., 1994, Ann. N.Y. Acad. Sci. 714: 211–224). In addition, in vitro cell models include but are not limited to monocytes exposed to low density lipoprotein (Frostegard et al., 1996, Atherosclerosis 121: 93–103), cloned vascular smooth muscle cells (Suttles et al., 1995, Exp. Cell Res. 218: 331–338), endothelial cell-derived chemoattractant exposed T cells (Katz et al., 1994, J. Leukoc. Biol. 55: 567–573), cultured human aortic endothelial cells (Farber et al., 1992, Am. J. Physiol. 262: 111088–1085), and foam cell cultures (Libby et al., 1996, Curr Opin Lipidol 7: 330–335). Potentially effective Therapeutics, for example but not by way of limitation, reduce foam cell formation in cell culture models, or reduce atherosclerotic plaque formation in hypercholesterolemic mouse models of atherosclerosis in comparison to controls.

Accordingly, once an atherosclerosis-associated disease or disorder has been shown to be amenable to treatment by modulation of activity or formation, that disease or disorder can be treated or prevented by administration of a Therapeutic that modulates activity.

Cytokine and Cell Proliferation/Differentiation Activity

An FCTRX protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK.

The activity of a protein of the invention may, among other means, be measured by the following methods: Assays for T-cell or thymocyte proliferation include without limitation those described in: CURRENT PROTOCOLS IN IMMUNOLOGY, Ed by Coligan et al., Greene Publishing Associates and Wiley-Interscience (Chapter 3 and Chapter 7); Takai et al., *J Immunol* 137:3494–3500, 1986; Bertagnoili et al., *J Immunol* 145:1706–1712, 1990; Bertagnolli et al., *Cell Immunol* 133:327–341, 1991; Bertagnolli, et al., *J Immunol* 149:3778–3783, 1992; Bowman et al., *J Immunol* 152:1756–1761, 1994.

Assays for cytokine production and/or proliferation of spleen cells, lymph node cells or thymocytes include, without limitation, those described by Kruisbeek and Shevach, In: CURRENT PROTOCOLS IN IMMUNOLOGY, Coligan et al., eds., Vol 1, pp. 3.12.1-14, John Wiley and Sons, Toronto 1994; and by Schreiber, In: CURRENT PROTOCOLS IN IMMUNOLOGY, Coligan eds., Vol 1, pp. 6.8.1-8, John Wiley and Sons, Toronto 1994.

Assays for proliferation and differentiation of hematopoietic and lymphopoietic cells include, without limitation, those described by Bottomly et al., In: CURRENT PROTOCOLS IN IMMUNOLOGY, Coligan et al., eds., Vol 1, pp. 6.3.1—6.3.12, John Wiley and Sons, Toronto 1991; deVries et al., *J Exp Med* 173:1205–1211, 1991; Moreau et al., *Nature* 336:690–692, 1998; Greenberger et al., *Proc Natl Acad Sci U.S.A.* 80:2931–2938, 1983; Nordan, In: CURRENT PROTOCOLS IN IMMUNOLOGY, Coligan et al., eds., Vol 1, pp. 6.6.1–5, John Wiley and Sons, Toronto 1991; Smith et al., *Proc Natl Acad Sci U.S.A.* 83:1857–1861, 1986; Measurement of human Interleukin 11-Bennett, et al. In: CURRENT PROTOCOLS IN IMMUNOLOGY, Coligan et al., eds., Vol 1, pp. 6.15.1 John Wiley and Sons, Toronto 1991; Ciarletta, et al., In: CURRENT PROTOCOLS IN IMMUNOLOGY, Coligan et al., eds., Vol 1, pp. 6.13.1, John Wiley and Sons, Toronto 1991.

Assays for T-cell clone responses to antigens (which will identify, among others, proteins that affect APC-T cell interactions as well as direct T-cell effects by measuring proliferation and cytokine production) include, without limitation, those described In: CURRENT PROTOCOLS IN IMMUNOLOGY, Coligan et al., eds., Greene Publishing Associates and Wiley-Interscience (Chapter 3, Chapter 6, Chapter 7); Weinberger et al., *Proc Natl Acad Sci USA* 77:6091–6095, 1980; Weinberger et al., *Eur J Immun* 11:405–411, 1981; Takai et al., *J Immunol* 137:3494–3500, 1986; Takai et al., *J Immunol* 140:508–512, 1988.

Immune Stimulating or Suppressing Activity

An FCTRX protein of the present invention may also exhibit immune stimulating or immune suppressing activity, including without limitation the activities for which assays are described herein. A protein are useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases caused by viral, bacterial, fungal or other infection may be treatable using a protein of the present invention, including infections by HIV, hepatitis viruses, herpesviruses, mycobacteria, Leishmania species, malaria species, and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased. Operationally, tolerance can be demonstrated by the lack of a T cell response under re-exposure to specific antigen in the absence of the tolerizing agent.

Down regulating or preventing one or more antigen functions (including without limitation B lymphocyte antigen functions (such as, for example, B7), e.g., preventing high level lymphokine synthesis by activated T cells, are useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to energize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc Natl Acad Sci USA, 89:11102–11105 (1992). In addition, murine models of GVHD (see Paul ed., FUNDAMENTAL IMMUNOLOGY, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and auto-antibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of auto-antibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosis in MRL/lpr/lpr mice or NZB hybrid mice, murine autoimmune collagen arthritis, diabetes mellitus in NOD mice and BB rats, and murine experimental myasthenia gravis (see Paul ed., FUNDAMENTAL IMMUNOLOGY, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function are useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigenpulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) are useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2 like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I a chain protein and $b_2$ microglobulin protein or an MHC class II a chain protein and an MHC class II b chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods: Suitable assays for thymocyte or splenocyte cytotoxicity include, without limitation, those described In: CURRENT PROTOCOLS IN IMMUNOLOGY, Coligan et al., eds. Greene Publishing Associates and Wiley-Interscience (Chapter 3, Chapter 7); Herrmann et al., *Proc Natl Acad Sci USA* 78:2488–2492, 1981; Herrmann et al., *J Immunol* 128:1968–1974, 1982; Handa et al., *J Immunol* 135:1564–1572, 1985; Takai et al., *J Immunol* 137:3494–3500, 1986; Takai et al., *J Immunol* 140:508–512, 1988; Herrmann et al., *Proc Natl Acad Sci USA* 78:2488–2492, 1981; Herrmann et al., *J Immunol* 128:1968–1974, 1982; Handa et al., *J Immunol* 135:1564–1572, 1985; Takai et al., *J Immunol* 137:3494–3500, 1986; Bowman et al., *J Virology* 61:1992–1998; Takai et al., *J Immunol* 140:508–512, 1988; Bertagnolli et al., *Cell Immunol* 133: 327–341, 1991; Brown et al., *J Immunol* 153:3079–3092, 1994.

Assays for T-cell dependent immunoglobulin responses and isotype switching (which will identify, among others, proteins that modulate T-cell dependent antibody responses and that affect Th1/Th2 profiles) include, without limitation, those described in: Maliszewski, *J Immunol* 144:3028–3033, 1990; and Mond and Brunswick In: CURRENT PROTOCOLS IN IMMUNOLOGY, Coligan et al., eds., Vol 1, pp. 3.8.1–3.8.16, John Wiley and Sons, Toronto 1994.

Mixed lymphocyte reaction (MLR) assays (which will identify, among others, proteins that generate predominantly Th1 and CTL responses) include, without limitation, those described in: CURRENT PROTOCOLS IN IMMUNOLOGY, Coligan et al., eds. Greene Publishing Associates and Wiley-Interscience (Chapter 3, Chapter 7); Takai et al., *J Immunol* 137:3494–3500, 1986; Takai et al., *J Immunol* 140:508–512, 1988; Bertagnolli et al., J Immunol 149; 3778–3783, 1992.

Dendritic cell-dependent assays (which will identify, among others, proteins expressed by dendritic cells that activate naive T-cells) include, without limitation, those described in: Guery et al., *J Immunol* 134:536–544, 1995; Inaba et al., *J Exp Med* 173:549–559, 1991; Macatonia et al., *J Immunol* 154:5071–5079, 1995; Porgador et al., *J Exp Med* 182:255–260, 1995; Nair et al., *J Virol* 67:4062–4069, 1993; Huang et al., *Science* 264:961–965, 1994; Macatonia et al., *J Exp Med* 169:1255–1264, 1989; Bhardwaj et al., *J Clin Investig* 94:797–804, 1994; and Inaba et al., *J Exp Med* 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., *Cytometry* 13:795–808, 1992; Gorczyca et al., *Leukemia* 7:659–670, 1993; Gorczyca et al., *Cancer Res* 53:1945–1951, 1993; Itoh et al., Cell 66:233–243, 1991; Zacharchuk, *J Immunol* 145:4037–4045, 1990; Zamai et al., *Cytometry* 14:891–897, 1993; Gorczyca et al., *Internat J Oncol* 1:639–648, 1992.

Assays for proteins that influence early steps of T-cell commitment and development include, without limitation, those described in: Antica et al., *Blood* 84:111–117, 1994; Fine et al., *Cell Immunol* 155: 111–122, 1994; Galy et al., *Blood* 85:2770–2778, 1995; Toki et al., *Proc Nat Acad Sci USA* 88:7548–7551, 1991.

Hematopoiesis Regulating Activity

An FCTRX protein of the present invention are useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g., in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In CULTURE OF HEMATOPOIETIC CELLS, Freshney et al. eds. Vol pp. 265–268, Wiley-Liss, Inc., New York, N.Y. 1994; Kirayama et al., *Proc Natl Acad Sci USA* 89:5907–5911, 1992; McNiece and Briddeli. In CULTURE OF HEMATOPOIETIC CELLS, Freshney, et al. eds. Vol pp. 23–39, Wiley-Liss, Inc., New York, N.Y. 1994; Neben et al., *Exp Hematol* 22:353–359, 1994; Ploemacher In CULTURE OF HEMATOPOIETIC CELLS, Freshney, et al. eds. Vol pp. 1–21, Wiley-Liss, Inc., New York, N.Y. 1994; Spoonceret al., In CULTURE OF HEMATOPOIETIC CELLS, Freshhey, et al., eds. Vol pp. 163–179, Wiley-Liss, Inc., New York, N.Y. 1994; Sutherland, In CULTURE OF HEMATOPOIETIC CELLS, Freshney, et al. eds. Vol pp. 139–162, Wiley-Liss, Inc., New York, N.Y. 1994.

Tissue Growth Activity

An FCTRX protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendonitis, carpal tunnel syndrome and other tendon or ligament defects. The compositions may also include an appropriate matrix and/or sequestering agent as a career as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, of for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing*, pp. 71–112 (Maibach, H I and Rovee, D T, eds.), Year Book Medical Publishers, Inc., Chicago, as modified by Eaglstein and Menz, J. Invest. Dermatol 71:382–84 (1978).

Activin/Inhibin Activity

An FCTRX protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, are useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-b group, are useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., *Proc Natl Acad Sci USA* 83:3091–2095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, cosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: CURRENT PROTOCOLS IN IMMUNOLOGY, Coligan et al., eds. (Chapter 6.12. Measurement of alpha and beta Chemokines 6.12.1–6.12.28); Taub et al. J Clin Invest 95:1370–1376, 1995; Lind et al. APMIS 103:140–146, 1995; Muller et al Eur *J Immunol* 25: 1744–1748; Gruberet al. *J Immunol* 152:5860–5867, 1994; Johnston et al. *J Immunol* 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell—cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., *Proc Natl Acad Sci USA* 84:6864–6868, 1987; Bierer et al., J. Exp. Med. 168:1145–1156, 1988; Rosenstein et al., J. Exp. Med. 169:149–160 1989; Stoltenborg et al., *J Immunol* Methods 175:59–68, 1994; Stitt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell—cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s): effecting behavioral characteristics, including, without limitation, appetite, libido, stress, cognition (including cognitive disorders), depression (including depressive disorders) and violet behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

This invention is further illustrated by the following examples, which should not be construed as limiting. The contents of all references, patents and published patent applications cited throughout this application are hereby incorporated by reference.

EXAMPLE 1

Identification of Murine Clone 7971c.7-r0s0-212.2-EXT (SEQ ID NO:2)

Differential gene expression was examined in mammary tumors that spontaneously arise between 1 and 5 months of age in Wnt-1 transgenic mice. Expression in mammary tumors was compared to the gene expression pattern found in the normal mammary gland of wild type age matched mice. The Wnt-1 transgenic mice were obtained from Genentech, Inc. (So. San Francisco, Calif.). Quantitative Expression Analysis (QEA) was performed on mRNA isolated from the tumor stage of progression in these mice (8 months). Sample preparation and QEA analysis are described fully in U.S. Pat. No. 5,871,697 an din Shimkets et al., Nature Biotechnology 17:198–803 (1999)), incorporated herein by reference in their entireties.

Figure 6:
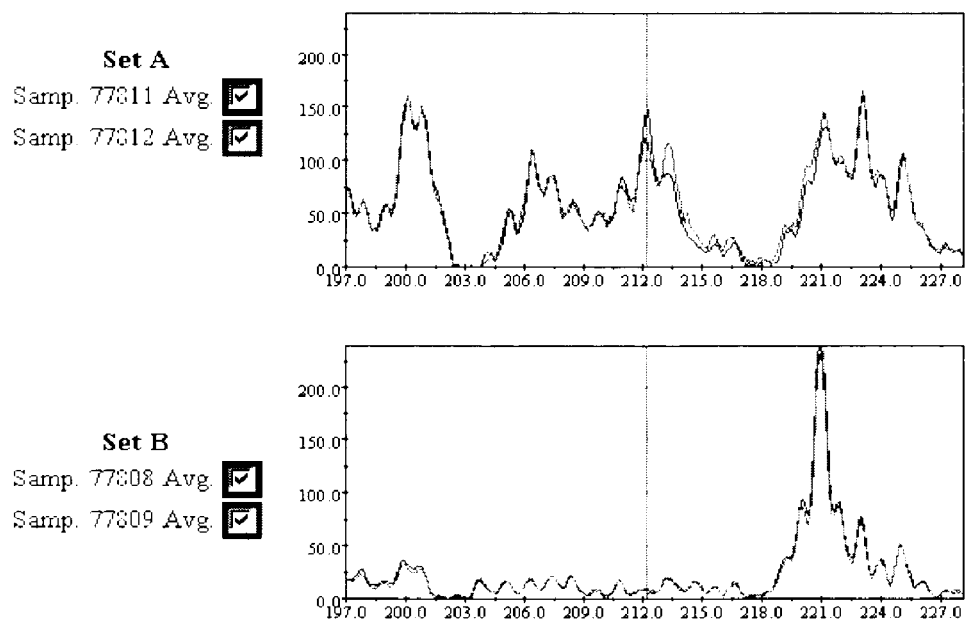
FIG. 6 is a representation of the differential gene expression in transgenic Wnt-1 mice (Set A) compared to wild type mice (Set B) detected by labeled fragments run in capillary electrophoresis.

Traces for two animals are shown in FIG. 6 for each of the two sets comparing transgenic mice to wild type mice. A series of transcripts overexpressed in the transgenic mice, including one at position 212.2 (vertical marker) was found. This band was designated as 7971c.7 (SEQ ID NO:1).

The sequence of murine clone 7971c.7 was extended by assembly with other murine nucleic acid fragments. The resulting assembly provided the sequence of clone 7971c.7-r0s0-212.2-EXT (SEQ ID NO:2).

EXAMPLE 2

Identification of Clone 65677221-3-frag (SEQ ID NO:5), a Novel Human S100 Cytokine Murine clone 7971c.7 was found to have high similarity to the human EST AA315020 (SEQ ID NO:4). This sequence includes two unspecified bases designated "N" in SEQ ID NO:4. EST AA315020 was assembled with human sequences present in CuraGen Corporation's sequence database obtained by its SeqCalling technology. SeqCalling is a differential expression and sequencing procedure that normalizes mRNA species in a sample, and is disclosed in U.S. Ser. No. 09/417,386, filed Oct. 13, 1999, incorporated herein by reference in its entirety.

This process was used to assemble the sequence of SEQ ID NO:5 encompassing the sequence of SEQ ID NO:4 (shown as the complementary strand, SEQ ID NO:49), including providing base calls for the two unidentified bases in SEQ ID NO:4. Three separate SeqCalling fragments were identified in this search (shown as assembly 65677221+ (SEQ ID NO:37)), two arising from embryonic tumor cell lines (CuraGen Nos. 61097801 and 61124196), and one from endothelial cells (primary dermal endothelial cell from Cell Application, San Diego, Calif.; CuraGen No. 60920173) that were treated with the cytokines IL-1beta (2 ng/ml) and TNF-alpha (5 ng/ml) for 16 hrs in order to induce leukocyte adherence. The alignment of the resulting assembly with the original EST AA315020 (SEQ ID NO:4) to provide the consensus sequence identified as SEQ ID NO:5 is shown in FIG. 7. This consensus was obtained using the CAP alignment program (Huang X, Genomics 1992 September; 14(1):18–25).

EXAMPLE 3

Quantitative Expression Analysis of Human Clone 65677221-3-frag (SEQ ID NO:5) in Various Cells and Tissues The quantitative expression of various clones was assessed in about 41 normal and about 55 tumor samples by real time quantitative PCR (TAQMAN®) performed on a Perkin-Elmer Biosystems ABI PRISM® 7700 Sequence Detection System.

First, 96 RNA samples were normalized to β-actin and GAPDH, RNA (~50 ng total or ~1 ng polyA+) was converted to cDNA using the TAQMAN® Reverse Transcription Reagents Kit (PE Biosystems, Foster City, Calif.; Catalog No. N808-0234) and random hexamers according to the manufacturer's protocol. Reactions were performed in 20 ul and incubated for 30 min. at 48° C. cDNA (5 ul) was then transferred to a separate plate for the TAQMAN® reaction using β-actin and GAPDH TAQMAN® Assay Reagents (PE Biosystems; Catalog Nos. 4310881E and 4310884E, respectively) and TAQMAN® universal PCR Master Mix (PE Biosystems; Catalog No. 4304447) according to the manufacturer's protocol. Reactions were performed in 25 ul using the following parameters: 2 min. at 50° C; 10 min. at 95° C.; 15 sec. at 95° C./1 min. at 60° C. (40 cycles). Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100. The average CT values obtained for β-actin and GAPDH were used to normalize RNA samples. The RNA sample generating the highest CT value required no further diluting, while all other samples were diluted relative to this sample according to their β-actin/GAPDH average CT values.

Normalized RNA (5 ul) was converted to cDNA and analyzed via TAQMAN® using One Step RT-PCR Master Mix Reagents (PE Biosystems; Catalog No. 4309169) and gene-specific primers according to the manufacturer's instructions. Probes and primers were designed for each assay according to Perkin Elmer Biosystem's Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature ($T_m$) range=58°–60° C., primer optimal Tm=59° C., maximum primer difference=2° C., probe does not have 5' G, probe $T_m$ must be 10° C. greater than primer $T_m$, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM. The primers and probe used are designated Probe Name Ag1526 and are shown in Table 7.

TABLE 7

Probe Name: Ag1526

| Primers | Sequences | $T_M$, ° C. | Length |
|---|---|---|---|
| Forward | 5'-CTTGATGAGGGTCTCAATGG-3' (SEQ ID NO:7) | 58.1 | 20 |
| Probe | FAM-5'-CCACATCACTGAATTCCTGAGCATCC-3'-TAMRA (SEQ ID NO:8) | 68.9 | 26 |
| Reverse | 5'-CAGACACAGTGAGCACCATG-3' (SEQ ID NO:9) | 58.8 | 20 |

PCR conditions: Normalized RNA from each tissue and each cell line was spotted in each well of a 96 well PCR plate (Perkin Elmer Biosystems). PCR cocktails including two probes (SEQX-specific and another gene-specific probe multiplexed with the SEQX probe) were set up using 1× TaqMan™ PCR Master Mix for the PE Biosystems 7700, with 5 mM MgCl2, dNTPs (dA, G, C, U at 1:1:1:2 ratios), 0.25 U/ml AmpliTaq Gold™ (PE Biosystems), and 0.4 U/µl RNase inhibitor, and 0.25 U/µl reverse transcriptase.-

Reverse transcription was performed at 48° C. for 30 minutes followed by amplification/PCR cycles as follows: 95° C. 10 min, then 40 cycles of 95° C. for 15 seconds, 60° C. for 1 minute.

The expression results are shown in Table 8.

TABLE 8

| Tissue_Name | Rel. Expr., % | Tissue_Name | Rel. Expr., % |
| --- | --- | --- | --- |
| Endothelial cells | 0.0 | Renal carcinoma 786-0 | 0.1 |
| Endothelial cells (treated) | 0.5 | Renal carcinoma A498 | 0.1 |
| Pancreas | 0.1 | Renal carcinoma RXF 393 | 0.0 |
| Pancreatic carcinoma CAPAN 2 | 13.9 | Renal carcinoma ACHN | 0.0 |
| Adrenal Gland (new lot*) | 0.0 | Renal carcinoma UO-31 | 0.0 |
| Thyroid | 0.8 | Renal carcinoma TK-10 | 0.3 |
| Salivary gland | 5.8 | Liver | 0.5 |
| Pituitary gland | 0.0 | Liver (fetal) | 1.9 |
| Brain (fetal) | 0.0 | Liver carcinoma (hepatoblast) HepG2 | 22.5 |
| Brain (whole) | 0.0 | Lung | 0.4 |
| Brain (amygdala) | 0.0 | Lung (fetal) | 1.2 |
| Brain (cerebellum) | 0.0 | Lung carcinoma (small cell) LX-1 | 12.2 |
| Brain (hippocampus) | 0.0 | Lung carcinoma (small cell) NCI-H69 | 2.8 |
| Brain (thalamus) | 0.0 | Lung carcinoma (small cell variant) SHP-77 | 0.0 |
| Cerebral Cortex | 0.1 | Lung carcinoma (large cell) NCI-H460 | 0.0 |
| Spinal cord | 0.3 | Lung carcinoma (non-small cell) A549 | 0.1 |
| CNS carcinoma (glioma/astrocytoma) U87-MG | 0.0 | Lung carcinoma (non-small cell) NCI-H23 | 0.0 |
| CNS carcinoma (glioma/astrocytoma) U-118-MG | 0.0 | Lung ca (non-small cell) HOP-62 | 0.0 |
| CNS carcinoma (astrocytoma) SW1783 | 0.0 | Lung carcinoma (non-small cell) NCI-H522 | 0.0 |
| CNS carcinoma* (neuroblastoma; metastasis) SK-N-AS | 0.0 | Lung carcinoma (squamous) SW 900 | 10.6 |
| CNS carcinoma (astrocytoma) SF-539 | 0.0 | Lung carcinoma (squamous) NCI-H596 | 1.4 |
| CNS carcinoma (astrocytoma) SNB-75 | 0.0 | Mammary gland | 0.5 |
| CNS carcinoma (glioma) SNB-19 | 0.0 | Breast carcinoma* (pleural effusion) MCF-7 | 63.1 |
| CNS carcinoma (glioma) U251 | 0.0 | Breast carcinoma* (pleural effusion) MDA-MB-231 | 0.0 |
| CNS carcinoma (glioma) SF-295 | 0.0 | Breast carcinoma* (pleural effusion) T47D | 0.6 |
| Heart | 1.6 | Breast carcinoma BT-549 | 0.0 |
| Skeletal Muscle (new lot*) | 0.0 | Breast carcinoma MDA-N | 0.0 |
| Bone marrow | 0.0 | Ovary | 0.2 |
| Thymus | 1.9 | Ovarian carcinoma OVCAR-3 | 2.8 |
| Spleen | 0.0 | Ovarian carcinoma OVCAR-4 | 79.9 |
| Lymph node | 0.0 | Ovarian carcinoma OVCAR-5 | 5.3 |
| Colorectal | 3.6 | Ovarian carcinoma OVCAR-8 | 0.1 |
| Stomach | 1.5 | Ovarian carcinoma IGROV-1 | 2.1 |
| Small intestine | 3.5 | Ovarian carcinoma* (ascites) SK-OV-3 | 0.9 |
| Colon carcinoma SW480 | 0.3 | Uterus | 0.2 |
| Colon carcinoma* (SW480 metastasis)SW620 | 4.3 | Placenta | 0.0 |
| Colon carcinoma HT29 | 12.0 | Prostate | 1.8 |
| Colon carcinoma HCT-116 | 31.4 | Prostate carcinoma* (bone metastasis)PC-3 | 0.4 |
| Colon carcinoma CaCo-2 | 44.2 | Testis | 0.0 |
| 83219 CC Well to Mod Diff (ODO3866) | 9.8 | Melanoma Hs688(A).T | 0.0 |
| Colon carcinoma HCC-2998 | 100.0 | Melanoma* (metastasis) Hs688(B).T | 0.0 |
| Gastric carcinoma* (liver metastasis) NCI-N87 | 37.8 | Melanoma UACC-62 | 0.0 |
| Bladder | 2.2 | Melanoma M14 | 0.0 |
| Trachea | 0.4 | Melanoma LOX IMVI | 0.0 |
| Kidney | 4.6 | Melanoma* (metastasis) SK-MEL-5 | 0.0 |
| Kidney (fetal) | 0.7 | Renal carcinoma 786-0 | 0.1 |

* = established from metastasis

The results in Table 8 indicate that the clone of SEQ ID NO:5 is very strongly expressed in several tumor derived cell lines compared with normal tissue, especially colon tumor cells, breast tumor cells and ovarian tumor cells. This observation indicates that the clone of SEQ ID NO:5 has a role in cell proliferation and potential utility as a blood marker to identify and/or stage tumors. It may furthermore be a target for a specific monoclonal antibody that could be used to treat various cancers, especially colon cancer, breast cancer and ovarian cancer.

OTHER EMBODIMENTS

Although particular embodiments have been disclosed herein in detail, this has been done by way of example for purposes of illustration only, and is not intended to be limiting with respect to the scope of the appended claims. In particular, it is contemplated by the inventor that various substitutions, alterations, and modifications may be made to the invention without departing from the spirit and scope of the invention as defined by the claims. Therefore, other aspects, advantages, and modifications are within the scope of the following claims.

What is claimed is:

1. An isolated polypeptide comprising the amino acid sequence of SEQ ID NO:3.

2. The polypeptide of claim 1, wherein the polypeptide is further fused to a heterologous polypeptide.

3. A composition comprising the polypeptide of claim 2 and a carrier.

4. A composition comprising the polypeptide of claim 1 and a carrier.

5. An isolated polypeptide consisting of an amino acid sequence wherein the amino acid sequence is SEQ ID NO:3.

6. The polypeptide of claim 5 further fused to a heterologous polypeptide.

7. A composition comprising the polypeptide of claim 5.

* * * * *

UNITED STATES PATENT AND TRADEMARK OFFICE
CERTIFICATE OF CORRECTION

| | | |
|---|---|---|
| PATENT NO. | : 7,005,499 B1 | Page 1 of 1 |
| APPLICATION NO. | : 09/715418 | |
| DATED | : February 28, 2006 | |
| INVENTOR(S) | : Lewin et al. | |

It is certified that error appears in the above-identified patent and that said Letters Patent is hereby corrected as shown below:

Title page, Item (56) References Cited, Other Publications: "Donato, R., "Funcational roles" should read --Donato, R., "Functional roles--

Brown et al. reference: "in breat cancer:" should read --in breast cancer:--

Col. 8, line 16: "in FIG. 1 is disclosed" should read --in FIG. 1 (SEQ ID NO:10) is disclosed--

Col. 8, line 18: "designated "G491246" is a" should read --designated "G491246" (SEQ ID NO:11) is a--

Col. 9, line 39: "in SEQ ID NO:4." should read --in SEQ ID NO:45.--

Col. 67, line 18: "SEQ ID NO:49)" should read --SEQ ID NO:48)--

Signed and Sealed this

Eighth Day of August, 2006

JON W. DUDAS
*Director of the United States Patent and Trademark Office*